(12) United States Patent
Braven et al.

(10) Patent No.: US 7,803,572 B2
(45) Date of Patent: Sep. 28, 2010

(54) PROTEASE DETECTION ASSAY

(75) Inventors: Helen Braven, Cardiff (GB); Russell Keay, Chippenham (GB); Stephen Flower, Bristol (GB)

(73) Assignee: Atlas Genetics, Ltd., Trowbridge (GB)

( * ) Notice: Subject to any disclaimer, the term of this patent is extended or adjusted under 35 U.S.C. 154(b) by 0 days.

(21) Appl. No.: 10/562,290

(22) PCT Filed: Jul. 9, 2004

(86) PCT No.: PCT/GB2004/002985

§ 371 (c)(1),
(2), (4) Date: Jun. 20, 2006

(87) PCT Pub. No.: WO2005/005657

PCT Pub. Date: Jan. 20, 2005

(65) Prior Publication Data

US 2006/0240503 A1    Oct. 26, 2006

(30) Foreign Application Priority Data

Jul. 9, 2003    (GB) ................................ 0316075.1

(51) Int. Cl.
*C12Q 1/37*    (2006.01)
*G01N 33/53*    (2006.01)
*G01N 27/26*    (2006.01)

(52) U.S. Cl. ...................... 435/23; 435/7.72; 205/777.5

(58) Field of Classification Search ........................ None
See application file for complete search history.

(56) References Cited

U.S. PATENT DOCUMENTS

| 4,304,853 | A | | 12/1981 | Nigretto et al. | |
|---|---|---|---|---|---|
| 4,456,337 | A | * | 6/1984 | Nicholson | .................... 359/273 |
| 4,978,610 | A | * | 12/1990 | Forrest et al. | ............ 205/777.5 |
| 6,235,494 | B1 | | 5/2001 | Hugli | |
| 6,495,336 | B1 | * | 12/2002 | Ludin et al. | .................... 435/13 |
| 2005/0221315 | A1 | * | 10/2005 | Braven et al. | .................... 435/6 |

OTHER PUBLICATIONS

Nagy et al. Screen-Printed Amerometric Microcell for Proline Iminopeptidase Enzyme Activity Assay; Biosensors and Bioelectronics, vol. 15 (2000) pp. 265-272.*
Kunugi, S., et al., Int. J. Biol. Macromol., 1992, pp. 210-214, vol. 14, August.
Hirayama, K., et al., Biochem. Biophys. Res. Comm., 1990, pp. 639-646, vol. 173, No. 2.
Jones, L.J., et al., Anal. Biochem., 1997, pp. 144-152, vol. 251.
Shinohara, H., et al. Sensors and Actuators B, 2000, pp. 144-146, vol. 65.
Nam, R.K., et al. J. Clin. Oncol., 2000, pp. 1036-1042, vol. 18, No. 5.
Black, M.H., et al., Clin. Cancer Res., 2000, pp. 467-473, vol. 6.
Fultz, M.L. and Durst, R.A., Analytica Chimica Acta, 1982, pp. 1-18, vol. 140.
Matayoshi, E.D., et al., Science, 1990, pp. 954-958, vol. 247.

* cited by examiner

*Primary Examiner*—Rebecca E. Prouty
*Assistant Examiner*—Paul C. Martin
(74) *Attorney, Agent, or Firm*—Bell & Associates; Matthew Kaser; Adam Warwick Bell

(57) ABSTRACT

The invention provides methods and compounds for detecting protease activity in a sample solution comprising contacting the sample solution with a protease substrate labelled with an electrochemically active marker, providing conditions under which any protease which may be present in the sample may degrade the protease substrate and electrochemically determining information relating to the electrochemically active marker.

12 Claims, 30 Drawing Sheets

A = Fc:BSA sample   B = BSA:FCA 20:1   C= BSA   D = FCA   E = BDSA:FCA 10:1

PROTEASE DETECTION ASSAY

RELATION TO OTHER APPLICATIONS

This is a national phase filing under 35 USC 371 of international application No. PCT/GB2004/002985 filed on 9 Jul. 2004 and published on 20 Jan. 2005 as WO 2005/005657 A1, and claims priority to and benefit of GB0316075.1 filed on 9 Jul. 2003, all of which applications and publications are explicitly incorporated by reference herein.

FIELD OF THE INVENTION

The invention relates to methods for the detection or assessment of protease activity, and to substrates and apparatus for use in such methods.

BACKGROUND OF THE INVENTION

Protease enzymes are involved in a variety of biological phenomena, for example, in protein activation and cell signalling. Protease activity plays a key role in processes such as blood clotting, apoptosis and hormone regulation. Proteases are also essential to the function of a variety of viral and microbial pathogens. There is an increasing interest in the development of protease inhibitors for use as therapeutic agents.

The determination of protease activity in biological samples is important in the analysis of processes such as apoptosis, in the screening of potential protease inhibitors and in the monitoring of sample purity, for example during protein purification. Protease enzymes hydrolyse amides and esters to produce peptides, single amino acids or labelled amino acid fragments depending on the structure of the substrate and the nature of the enzyme. The determination of protease activity may be performed using either a naturally occurring protein substrate or a synthetic peptide substrate analogue that is labelled, for example with a fluorophore or a chromophore. The determination of protease activity may also be performed using a labelled short synthetic peptide that optionally incorporates a protease recognition sequence. In some cases the determination of protease activity may be performed using a labelled single amino acid. In these cases protease activity is detected by the ability of the protease to cleave the bond between the single amino acid and the marker with which it is labelled.

The nature of the protein used depends on the solubility required and the particular requirements of the assay; bovine serum albumin (BSA) or casein are commonly used. Gelatin, ovalbumin and cross-linked proteins have also been used.

Most detection assays on the market use a labelled substrate analogue. The detection of protease activity can be performed using a homogenous or a heterogenous reaction set up. In a homogenous detection assay, the substrate is typically in solution and the product is also in solution. Fluorescence-based detection systems using fluorophores (for example fluoroscein, rhodamine or BODIPY fluorophores) generally operate according to one of two principles: detection of a fluorescent signal following cleavage of a multiply labelled self-quenched protein (ENZCHEK protease assay kits, Molecular Probes Inc.), or detection of a change in the size of the fluorescent-labelled moiety/conjugate using fluorescence polarization techniques (BEACON protease activity detection kit, PanVera Corporation, ENZCHEK polarization kit, Molecular Probes Inc.).

In one commonly practised method, a peptide substrate is used that is labelled at the carboxyl terminus with a dye possessing an amine functionality. Such a dye may be a chromophore or a fluorophore, for example coumarin, fluoroscein, rhodamine or BODIPY (Molecular Probes Inc, APOALERT, CPP32 protease assay kits, Clontech). The amide bond that couples dye and amino acid is cleaved by the protease to produce an amine derivative. That change in structure affects the spectral characteristics of the dye and a detectable signal is thus produced. An alternative strategy for homogenous detection is to use a peptide substrate that is labelled at one side of a cleavage site with a donor fluorophore and at the other side with an acceptor quencher, which together form a fluorescence resonance energy transfer (FRET) pair. Cleavage of the peptide results in separation of the donor and acceptor and therefore produces a change in fluorescence signal. Hydrolysis of a specific peptide sequence can be detected by a gel based analysis (PEPTAG protease assay, Promega).

A heterogenous assay typically involves the cleavage of a dye-labelled fragment of an immobilised substrate and subsequent analysis of the liquid phase (PROTEASESPOTS, Jerini AG, PROCHECK Universal Protease Assay, Intergen).

Protease activity may also be determined using an unmodified (i.e. naturally occurring) protein substrate. Assays using unmodified protein substrates generally require precipitation of the undigested substrate and subsequent detection of cleaved protein fragments. Such detection can be, for example, by measurement of absorbance at 278 nm, or by detection of the resulting primary amine functionality. Such methods often lack sensitivity, require sampling to obtain kinetic data and depend on quantitative precipitation for accurate results. Alternatively, hydrolysis of succinylated proteins may be detected following reaction of the resulting peptide fragments with TNBSA (trinitrobenzenesulfonic acid).

Except where the contrary is apparent from the context, the term "substrate" is used throughout the remainder of this document to include both naturally occurring substrates and synthetic substrates. Synthetic substrates include synthetic analogues of naturally occurring substrates, synthetic peptides incorporating a protease recognition sequence, and other synthetic peptides, and single amino acids. Single amino acids are regarded as a substrate because, although they lack an internal bond capable of being cleaved by a protease enzyme, such a bond may be formed through the attachment of a marker.

The term "protease" as used herein is intended to include within its scope proteins that are known as proteinases.

The terms "peptide" and "protein" are used interchangeably herein and both include amino acid sequences of any length including those with a small number of amino acid residues, for example five residues or three residues. The terms "peptide" and "protein" include both molecules made in cells and molecules made by cell-free synthesis. The terms "peptide" and "protein" include molecules having naturally occurring, semi-synthetic or artificial sequences, which sequences may include amino acids that do not occur naturally in proteins. For example, the terms "peptide" and "protein" refer to an amino acid sequence of a recombinant or non-recombinant peptide having an amino acid sequence of (i) a native peptide, (ii) a biologically active fragment of a native peptide, (iii) a biologically active peptide analogue of a native peptide, (iv) a biologically active variant of a native peptide, (v) a peptide having an artificial sequence comprising a biologically active consensus sequence, or (vi) a peptide having a wholly artificial sequence.

The term "amino acid" includes naturally occurring amino acids and amino acids that do not occur naturally in proteins. It also includes amino acid derivatives, for example acylated amino acids, protease enzymes, hydrolyse amides, and esters. It will therefore be understood that a key requirement of a labelled protease substrate is the presence of bonds capable of being hydrolysed by protease enzymes. In general, therefore, the terms "protein", "peptide" and "amino acid" are to be interpreted broadly to encompass any derivative molecules that provide one or more bonds capable of being hydrolysed by protease enzymes. These hydrolysable bonds may be provided within the structure of the molecule itself or alternatively or additionally may be formed when the molecule is labelled by the attachment of a marker.

SUMMARY OF THE INVENTION

The invention provides a method of detecting protease activity in a sample comprising contacting a sample solution with a protease substrate labelled with an electrochemically active marker, providing conditions under which any protease which may be present in the sample may degrade the protease substrate, and electrochemically determining information relating to the electrochemically active marker. The information relating to the marker is expediently used to derive information concerning the presence or absence of protease activity. Preferably the electrochemical information may be used to quantify relative proportions of degraded and non-degraded substrate. As used herein the term "degrade" includes any degradation as a result of enzyme activity, for example by digestion. As used herein, the term "degrade" includes the cleavage of the marker from the labelled substrate even if there is no cleavage within the substrate molecule itself.

The modification of various biological molecules with a redox active label is known. Ferrocene is a commonly used label for such purposes because of its stability and its electrochemical properties and because of the availability of suitable ferrocene derivatives. For example a ferrocene modified glucose oxidase in which ferrocene is covalently attached to the surface of glucose oxidase via a spacer molecule was synthesised and that modified enzyme was found to allow for more efficient electron transfer between the enzyme and the mediator (International Journal of Biological Macromolecules (1992) 14(4), 210-214). Ferrocene has also been used to label proteins so as to facilitate their detection by voltammetric methods (for example, BSA, avidin or cytochrome P450). Ferrocenylated biological molecules for conjugation with a second molecule are also known, for example ferrocene-labelled digoxin antibody, ferrocene-labelled anti-HCG IgG and ferrocene-labelled biotin.

Labelling of proteins, peptides or amino acids with ferrocene may be performed for example by covalent attachment of an amine-, carboxyl- or sulfhydryl-reactive ferrocene derivative with specific amino acid residues of the protein. The examples of ferrocene derivatives developed to date include diamides, succinimidyl esters, aldehydes, primary amines, iodoacetamides and maleimides. Known methods of labelling proteins with electrochemically active markers involve labelling of amino groups of the proteins. The present invention provides methods of labelling proteins, peptides and amino acids which include methods of labelling via one or more carboxyl groups and also novel labels suitable for labelling via one or more amino groups. The provision of methods for labelling proteins, peptides and amino acids via a carboxyl group provides the advantage of allowing the production of labelled substrates having a free, underivatised amino terminal which may be required in order to develop working assays for certain amino peptidases which are a class of proteases which degrade peptides from the amino terminal.

DETAILED DESCRIPTION

The application of electrochemical detection to protease assays has a number of advantages over fluorescent detection. Electrochemical detection has the potential for very high levels of sensitivity and exhibits a wider linear dynamic range than fluorescence. There is no requirement for samples to be optically clear. There is also less interference from background contaminants (many biological samples auto fluoresce).

The present invention is based on the observation that an electrochemically active marker exhibits different electrochemical characteristics depending on whether or not it is attached to an amino acid residue, on whether or not that amino acid residue is incorporated into a peptide or protein, and on the length of any such peptide or protein.

Under appropriate circumstances, the electrochemical activity of a marker can change by a detectable degree following loss of attachment of a single or very few amino acid residues.

The size and characteristics of a molecule to which an electrochemically active marker is attached influence the observable characteristics of the electrochemical marker. That may occur, for example, by influencing the rate of migration of the marker by diffusion or its rate of migration in response to an electric field.

Electrochemical activity of a marker may also be influenced by steric effects resulting from the presence of the molecule to which it is linked. For example, steric hindrance may prevent the marker from approaching an electrode and accepting or donating electrons.

If the marker is attached to a peptide then the secondary structure of the peptide (as largely determined by the primary sequence) may influence the physical properties of the marker. For example, if the marker is attached to an amino acid residue in a peptide such that the structure of the peptide sterically hinders the electrochemically active marker then the signals observable by voltammetry may be reduced. Digestion of the peptide may destroy or release secondary structure elements and thus reduce or abolish the influence of the peptide structure on the marker. Accordingly, digestion of the peptide results in a change, usually an increase, in the electrochemical signal produced by the marker moiety. In a differential pulse voltammetry experiment, the faradaic current response at a particular applied voltage may increase upon digestion of the peptide.

It will be understood by the person skilled in the art that, because the secondary structure of a peptide is dependent on temperature, the effects the peptide has on an electrochemically active marker varies with temperature. The person skilled in the art is able to select a temperature at which to carry out the electrochemical technique of the invention in order to achieve an optimal signal to background noise ratio for the technique. If the technique is incorporated into an assay in which heating or cooling is performed, a measurement at a desired temperature can simply be obtained by selecting an appropriate point in the temperature regime to make the measurement.

The information relating to the electrochemically active marker can be obtained by voltammetry or by an amperometric method. Differential pulse voltammetry is particularly suitable. If desired, the electrochemical detection step may be carried out using one or more electrodes covered by a membrane which is able selectively to exclude molecules based on one or more characteristics, for example size, charge or hydrophobicity. That may assist in eliminating background noise current arising from, for example, charged species in the solution.

Suitable electrochemically active markers include those comprising metallo-carbocyclic pi complexes, that is organic complexes with partially or fully delocalised pi electrons. Suitable markers include those comprising sandwich moieties, in which two carbocyclic rings are parallel, or bent sandwich compounds (angular compounds) and monocyclopentadienyls. Preferably the electrochemically active marker is a metallocenyl label. More preferably it is a ferrocenyl label.

The ferrocene or metallocene ring, which preferably constitutes the labelling moiety, may be unsubstituted. If desired, the ferrocene or metallocene ring structure may be substituted by one or more substituents, the nature and location of which are selected so as to influence in a desired manner the redox characteristics of the ferrocene or metallocene moiety. The ferrocene or metallocene ring may additionally or instead be substituted by any ring substituents that do not materially reduce the electrochemical sensitivity of the label. Ferrocenyl and metallocenyl markers may advantageously be N-substituted ferrocene or metallocene carboxamides, or ferrocenylamines or metallocenylamines. The ferrocene or metallocene carboxamide moiety may be linked via the carboxamide nitrogen to the protein or peptide. Linkage to the protein or peptide can be by any suitable linkage, typically by linkage to an amino acid side chain. Where linkage is via an amine group of an amino acid, peptide or protein, the nitrogen atom may constitute the nitrogen of the carboxamide moiety. Where linkage is via a carboxyl group of an amino acid, peptide or protein, the ferrocenylamine or metallocenylamine labelling moiety may become a ferrocenylamide or metallocenylamide moiety following attachment to a carboxyl group of an amino acid, peptide or protein. When the unlabelled substrate does not in itself contain a bond capable of hydrolysis by the intended protease enzyme, for example, where the unlabelled substrate is a single amino acid, linkage of the substrate to the electrochemical marker is required to be such that it results in the formation of a bond capable of hydrolysis by the intended protease enzyme. In those circumstances labelling of the substrate would preferably be performed by covalent attachment to an amine- or carboxyl-reactive moiety of the substrate. Various synthetic methods have been developed for the derivatisation of protein, peptide or amino acid side chains or protein, peptide or amino acid terminal moieties. For example, lysine residues in a protein may be derivatised by reaction with a succinimidyl ester. For derivatisation at other amino acid residues, other known synthetic methods may be used. For example, a maleimide reagent may be used to derivatise cysteine residues. An N-hydroxy succinimide ester may be used to derivatise the amino terminus or side chain amino group of a protein or peptide, or an amino moiety of an amino acid.

The marker group may be attached to the protein, peptide or amino acid substrate through a linker moiety. There may be used any suitable linker moiety. Suitable linker moieties may comprise an aliphatic chain which may be linear or branched, and saturated or unsaturated. Advantageously, when labelling a protein, the linker moiety is a linear or branched aliphatic chain, for example an alkylene chain, having from 4 to 20 carbon atoms, and preferably from 6 to 16, especially from 8 to 14 atoms, especially 12 carbon atoms. The alkylene chains may be substituted by any substituent or may be interrupted by any atom or moiety provided that any such substituent, atom or moiety does not materially reduce the electrochemical sensitivity of the marker. Without wishing to be bound by theory, it appears that the linker moiety reduces the extent to which the tertiary structure of a protein substrate sterically interferes with the marker group and vice versa. This theory is consistent with the observation that, when the substrate is a single amino acid or a short peptide, for example, a tripeptide, that is to say a substrate molecule without a significant amount of tertiary structure, use of a linker moiety is generally not required.

Illustrative of the ferrocenyl labels which may be used in accordance with the invention are those in Formulae I, II and III. In formulae Ia and IIa, the labels of formula I and II are shown respectively attached to the side-chain amino group of a lysine amino acid residue of a peptide. In formula IIIa, the label shown in formula III is shown attached to the amino acid alanine. In formula IIIb, the label shown in formula III is shown attached to an Ala-Ala-Ala tripeptide. It can be seen from formula IIIb that the amino terminus of the alanine tripeptide moiety is acylated. The acyl group, indicated in abbreviated form by "Ac", was added to the tripeptide during the synthesis of the molecule shown in formula IIIb in order to protect the potentially reactive amino terminal of the tripeptide. In order to synthesise some of the labelled substrate molecules of the invention, protecting groups such as BOC (butoxycarbonyl) and acyl may need to be added to the substrate molecule. Such protecting groups may optionally be removed at a later stage of the synthesis. In certain circumstances, however, it may be more convenient to retain such groups so long as their presence does not materially reduce the utility of the molecule in the intended assay.

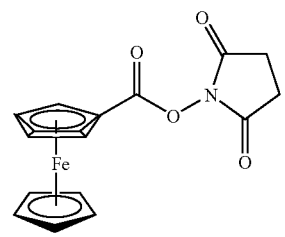

Formula I

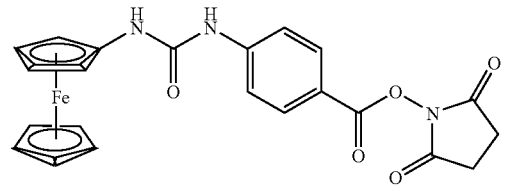

Formula II

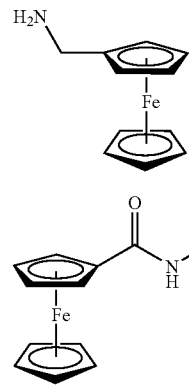

Formula III

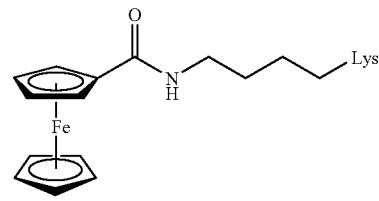

Formula Ia

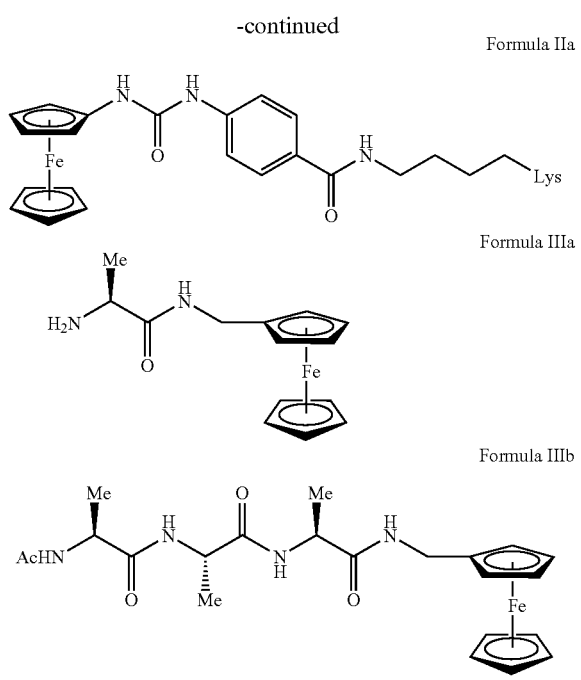

Formula IIa

Formula IIIa

Formula IIIb

In the case of a peptide or protein substrate with significant secondary structure, the synthesis of a labelled protein or peptide starting from a labelling moiety and the appropriate protein or peptide does not generally result in the complete derivatisation of the protein or peptide. Many sites are not accessible to reagents in solution. For example, the BSA molecule comprises 60 lysine residues (Hirayama et al., *Biochem. Biophys. Res. Commun.*, 1990, 173, 639-646). According to the literature, labelling of BSA with succinimidyl esters has given BSA:label ratios of between 1:5 and 1:23 (Jones, L. J. et al., *Analytical Biochem.*, 1997, 251, 144-152 and Hiroaki, S. et al., Sensors and Actuators B, 2000, 65, 144-146.). Generally the reaction product of a labelling synthesis contains a mixture of different product molecules with different numbers of markers. The average number of labels can be assessed by various spectroscopic methods, for example UV-visible spectroscopy. The distribution of the numbers of markers per protein molecule can be assessed more precisely by use of mass spectrometry.

The precise number of marker moieties present on a protein or peptide is not critical to the success of the assay of the invention. For good sensitivity, there are preferably on average several marker moieties on each protein or peptide molecule. However, when the substrate is a single amino acid or a short peptide, for example, a tripeptide, a single marker moiety on each substrate molecule is usually sufficient. Indeed, some small substrate molecules may only contain a single group which is suitable for labelling with a marker moiety. For use in assays with enzymes that cleave only particular amino acid sequences, it is preferable that a marker moiety is located relatively close to the cleavage site such that the marker's immediate environment is affected by the cleavage and its observable electrochemical properties are affected. Labelled short synthetic peptides and labelled single amino acids may be the preferred substrate types for certain protease enzyme assays, especially assays of enzymes such as amino peptidase and endopeptidases. In general, the use of labelled large proteins such as BSA or casein is preferred for use in assays for general protease activity. This is because large proteins will usually contain a variety of cleavage stiles including at least some capable of being recognised by many of the protease enzymes in the sample being assayed.

The use of short peptides is preferred under certain circumstances because it allows the synthesis of substrates containing only the recognition sequences specific for the specific protease or class of proteases under investigation. For example, a substrate incorporating a short peptide of the sequence Ala-Ala-Phe or Ala-Ala-Pro-Phe (SEQ ID NO: 1), and preferably very little or no further sequence, may be used in a specific assay for chymotrypsin activity. As a further example, Leucine aminopeptidase (LAP) is a proteolytic enzyme that is an exopeptidase that hydrolyses peptide bonds adjacent to a free amino group. It shows specificity for peptide bonds next to leucine residues. Elevated serum and urine levels of LAP are seen in several clinical conditions including cholestasis, hepatic cirrhosis, hepatic necrosis, hepatic tumor, breast cancer, endometrial cancer, ovarian cancer, systemic lupus erythematosus and germ cell tumors of the ovary and testis. A substrate comprising a short peptide containing N-terminal alanine residues or a substrate comprising a labelled alanine amino acid, for example the substrate shown in formula IIIa, may be used to screen serum or urine samples for elevate levels of LAP in order to assist diagnosis of one of the above-listed conditions.

Other clinical conditions associated with elevated serum levels of specific proteases include prostate cancer associated with elevated serum glandular kallikrein-2 protease (see Nam et al. *J. Clin. Oncol.* (2000) 18(5):1036-42) and prostate and breast cancer associated with elevated prostate-specific antigen (PSA) a serine enzyme (Black et al. *Clin. Cancer. Res.* (2000) 6(2):467-73).

The in vivo substrates of many proteases are proteins comprising several hundred amino acid residues. Whilst use of a substrate analogue that is a full length peptide (that is, is of length the same as or similar to that of a substrate for which it is an analogue) may be useful in some circumstances. For example, an analogue which is of similar length to a naturally occurring substrate for which it is an analogue might be expected to have characteristics (such as stability and conformational characteristics) which are more similar to those of the natural substrate than would be those of a much shorter analogue, and might therefore more accurately mimic the behaviour of the natural substrate.

In many circumstances, however, it is not essential for a full length protein to be used. According to one embodiment of the invention the peptide preferably comprises at least 5, more preferably at least 20 amino acid residues. For example, the peptide may comprise from 20 to 100 amino acid residues; most preferably the peptide comprises from 20 to 50 amino acid residues. According to another embodiment of the invention, the substrate preferably comprises a single amino acid molecule. According to yet another embodiment of the invention, the substrate comprises a peptide from having little or nothing more than the protease recognition sequence. Such recognition sequences are often 2 to 6 amino acid residues in length, more preferably 3 amino acids in length. In practice, the length of the peptide is so selected that there is present at least one cleavage site for the enzyme or enzymes of interest. Preferably the peptide has one different cleavage site for the enzyme or enzymes of interest. For example, Factor Xa protease requires the presence of the recognition sequence Ile-Glu-Gly-Arg (SEQ ID NO: 2) in its substrate. Peptides having more than one cleavage site may be of use, for example, where the substrate is to be used in a screen for general protease activity.

The method of the invention may be used to offer a qualitative measure of the protease activity in an unknown sample. The amount of protease activity may be quantified, for example, with use of a calibration curve obtained with standard solutions. If the identity of the protease present in a sample is known, the concentration of the protease may be calculated.

The invention further provides a protease assay kit comprising a protease substrate labelled with an electrochemically active marker. Such a kit may also comprise further reagents, for example appropriate solutions. The kit may also comprise instructions for carrying out a protease determination.

The invention also provides novel alternative electrochemically active labelled proteins or peptides. In a first embodiment, the invention accordingly provides compounds of formula IV,

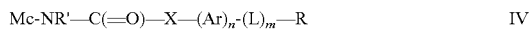

$$\text{Mc-NR'}-\text{C}(=\text{O})-\text{X}-(\text{Ar})_n-(\text{L})_m-\text{R} \quad\quad\quad \text{IV}$$

wherein
Mc is a metallocenyl group in which each ring may independently be substituted or unsubstituted,
the metallocenyl group comprises a metal ion M selected from the group consisting of iron, chromium, cobalt, osmium, ruthenium, nickel and titanium,
R' is H or lower alkyl,
X is either NR' or O,
Ar is a substituted or unsubstituted aryl group,
n is 0 or 1,
L is a linker group,
m is 0 or 1, and
R is a protein, peptide or amino acid residue.

In a second embodiment the invention provides a compound comprising a metallocenyl group attached to a carboxyl group of an amino acid residue, peptide or protein. The carboxyl group may be a terminal or side-chain carboxyl group.

Preferably the compound is of formula V,

$$\text{Mc-}(\text{CH}_2)_n-\text{X}-\text{R} \quad\quad\quad \text{V}$$

wherein
Mc is a metallocenyl group in which each ring may be independently substituted or unsubstituted,
the metallocenyl group comprises a metal ion M selected from the group consisting of iron, chromium, cobalt, osmium, ruthenium, nickel and titanium,
n is 1, 2, 3, 4, 5, 6, 7, 8, 9, 10, 11 or 12,
X is either NR' or O, and
R' is H or lower alkyl.
R is a protein, peptide or amino acid residue.

Metallocene (for example, ferrocene) groups, including Mc groups according to formula IV or formula V may be substituted by one or more groups selected from lower alkyl (for example $C_1$ to $C_4$ alkyl); lower alkyl substituted with a hydroxy, halo, cyano, oxo, amino, ester or amido or a further metallocene group; lower alkenyl; lower alkenyl substituted with a hydroxy, halo, cyano, oxo, amino, ester or amido, or a further metallocene group; aryl; or aryl substituted with a hydroxy, halo, cyano, oxo, amino, ester or amido, or a further metallocene group. The further metallocene group, if present, may be substituted in the same way as the Mc group with the exception that the total number Mc groups in the molecule of the invention preferably does not exceed four. Preferably, the Mc group is unsubstituted.

Preferably, M is an ion selected from iron, osmium and ruthenium. Most preferably, M is an iron ion. When M is an iron ion, Mc is a ferrocene.

Lower alkyl is preferably C1 to C4 alkyl. Preferably, R' is H. Each R' has an identity separate from the other R'.

Preferably X is NH.

The Ar group in formula IV preferably has at least 5, and for example from 5 to 10, ring carbon atoms, with $C_6$-aryl being preferred. The Ar group may be substituted by one or more groups selected from lower alkyl (for example $C_1$ to $C_4$ alkyl); lower alkyl substituted with a hydroxy, halo, cyano, oxo, amino, ester or amido group; lower alkenyl; lower alkenyl substituted with a hydroxy, halo, cyano, oxo, amino, ester or amido group; aryl; and aryl substituted with a hydroxy, halo, cyano, oxo, amino, ester or amido group. Preferably, the Ar group is unsubstituted. For example Ar may be phenylene Preferably, n=1. Preferably, m=1 in formula IV. In one preferred embodiment of the compound of formula IV, n=1 and m=1.

Suitable linker groups for use in the compound of formula IV (shown in formula IV as "L") include any moiety that is suitable for linking an amino group of a protein to an adjacent Ar or X group, respectively, and the selection of such groups would be a matter of routine for those skilled in the art. By way of example, the linker group L may be carbonyl, or may be an aliphatic chain which may be linear or branched, and saturated or unsaturated. Advantageously, the linker moiety is a linear or branched aliphatic chain having from 1 to 20 carbon atoms, preferably with at least 4 carbon atoms, and more preferably from 6 to 16, especially from 8 to 14 atoms, more especially 12 carbon atoms. The linker moiety may be an alkylene chain which may be substituted by any substituent or may be interrupted by any atom or moiety provided that any such substituent, atom or moiety does not materially reduce the electrochemical sensitivity of the label.

Specific preferred embodiments are those compounds illustrated in formulae IIa, IIIa and IIIb.

Preferably, R is a protein or a peptide from 2 to 1000 amino acid residues in length. For example, R may be a peptide of 3 amino acid residues in length or a peptide of from 2 to 40 amino acids in length or a peptide of from 40 to 1000 amino acids in length. In an alternative preferred embodiment, R is an amino acid. Preferably, R is a protein that is a substrate for a protease enzyme. In a preferred embodiment, R is BSA, or casein. Other suitable protease substrates may include gelatine, elastin, collagen and ovalbumin, fluorescently labelled forms of each of which are available from Molecular Probes, Inc.

Alternatively, R may be a naturally occurring or artificial amino acid.

In one class of labelled substrate in accordance with the invention, the marker moiety is attached to an amino group which is contained within a pendant side chain of a protein, and is preferably at the free amino terminus of that pendant side chain. That side chain may be a side chain which is part of a naturally occurring amino acid in which it is present. Thus, in Formula IIa above, the —NH—$(CH_2)_4$-chain is derived from the $NH_2(CH_2)_4$-chain which is inherently present in lysine. It will be appreciated, however, that a suitable pendant side chain may if desired be synthetically introduced into any desired location in the protein.

Another class of labelled substrate in accordance with the invention, the marker moiety is attached to a carboxyl group which is contained within the pendant side-chain of a protein and is preferably at the free carboxyl terminus of that pendant side-chain. That side-chain may be a side-chain of a naturally occurring amino acid. It will be appreciated, however that a substrate pendant side-chain may, if desired, be synthetically introduced into any desired location in the protein.

In one preferred class of labelled proteins, illustrated by formula IIa above:

Mc is ferrocenyl, R' is H, X is —NH—, Ar is phenylene, L is carbonyl and n=m=1, and R presents a protein in which the marker moiety is attached to the protein backbone via a pendant side chain of a lysine residue.

In another class of labelled substrate in accordance with the invention, the marker moiety may be attached via the terminal amino group of a protein or amino acid, and in that case it will normally be preferred for L to have a minimum of four carbon atoms, preferably comprising a carbonyl group which in the labelled protein combines with the protein terminal amine group to form a carboxamide moiety.

In another class of labelled substrate in accordance with the invention, the marker moiety may be attached via the terminal carboxyl group of a protein or amino acid.

In a yet further class of labelled protein in accordance with the invention, the marker moiety is attached via a pendant side chain which has been synthetically attached to the protein backbone and in that case L will normally comprise a chain of minimum of four carbon atoms having at one end of said chain, or being interrupted by, a carboxamide moiety.

The compound of the invention may comprise more than one metallocene groups. Typically, several metallocene groups are attached to the same protein or peptide molecule. For example, in the case of BSA, there may be 10 to 20 metallocene groups per BSA molecule. In the compound of the invention, the metallocene group may be substituted by any other electrochemically active marker group. The compound of the invention may be one which is electrochemically active or becomes electrochemically active following partial cleavage.

However, if the labelled substrate is relatively small, for example if it contains a single amino acid or a short peptide, for example a tripeptide, it may not be necessary or feasible for the substrate to comprise multiple marker moieties.

Compounds of the invention may be prepared by reaction of a metallocene compound comprising a suitable functional group with a protein, peptide or amino acid.

For example, an N-hydroxysuccinimide ester of a metallocene derivative may be used. Details of the use of such a compound to label a peptide are provided in Examples 2, 3 and 4a. N-hydroxysuccinimide esters are suitable for attachment of a marker to lysine side chains. Alternatively, a metallocenemethyl amine, for example ferrocene methylamine, may be used. Details of the use of such a compound to label an amino acid and a peptide are provided in Examples 4b and 4c. It will however be apparent to the skilled person that similar labels may be attached to a peptide at any suitable side chain by use of an appropriate labelling functional group.

Compounds in accordance with the invention have particular utility in methods according to the invention. Under the conditions set out in table 1, substituted ferrocene carboxylic acids have an electrode potential in the region of 400 mV. On the other hand, substituted metallocene compounds in accordance with the invention have an electrode potential in the region of 150 mV. The lower potential is a potential at which the propensity for background impurities to interfere with data collection is much lower. Accordingly, the compounds of the invention enable more sensitive readings to be taken. In FIG. 12 there are shown voltammograms of digestion of a 4-(3'-ferrocenylureido)-1-benzoyl labelled BSA molecule; in FIG. 3, there are shown voltammograms of digestion of a ferrocenyl labelled BSA molecule under the same reaction conditions. As is seen from a comparison of FIGS. 12(c) and 3(c) the peak for the 4-(3'-ferrocenylureido)-1-benzoyl derivative with a ferrocene moiety as found in molecules of the invention comes at around 100 mV, whereas the peak for the ferrocenyl derivative comes at around 400 mV.

The invention also provides methods of diagnosing or monitoring a disease in a subject comprising using a method of the invention in the detection of a protease or a protease inhibitor associated with said disease in a tissue or body fluid of the subject.

Furthermore, the invention provides use of a method of the invention for detecting a disease in a subject.

Examples of disease that are associated with the presence of a protease or a protease inhibitor in a tissue of the subject include hereditary predisposition to thromoembolism caused to deficiencies in anti-thrombin III in the blood serum. Elevated serum or extracellular matrix cathepsin levels may be indicative of Alzheimer's, cancer or arthritis. Preferably the tissue or body fluid of the subject is serum, plasma, saliva or urine or any other tissue or body fluid of which a sample may be conveniently and safely obtained.

The invention also provides methods of detecting a pathogen or other undesirable organism, for example a food spoilage organism, comprising using a method of the invention in the detection of a protease or protease inhibitor associated with said pathogen or undesirable organism in a sample. Furthermore, the invention provides use of a method of the invention for detecting a pathogen or other undesirable organism in a sample. For example, *Cochliobolus heterostrophus* is a maize leaf spot pathogen that may be diagnosed in a plant by detection of specific proteases in a sample of infected maize leaf. Many other pathogens are associated with specific proteases, for example the serine protease Alp in the lung fluid of humans infected with *Aspergillus fumigatus* and the HIV-1 protease PT in leucocytes of humans infected with HIV-1.

The invention also provides methods of screening from protease inhibitors. Such methods may be used in screening putative protease inhibitors in order to identify novel compounds of clinical interest.

The invention also provides apparatus arranged to carry out any one or more of the methods disclosed herein. Such apparatus may include suitable electrodes, electrochemical cells, disposable plastic ware and apparatus for detecting, recording, manipulating and displaying results. A thermostat and/or heating device may also be included.

The invention provides apparatus comprising one or more sample receiving regions for receiving one or more samples, means for controlling the temperature of said sample receiving regions and means for measuring the electrochemical properties of said sample. Such an apparatus may be manufactured so as to utilize conventional electrode cells (for example those used in examples herein).

The present invention further provides a container comprising one or more sample receiving regions for holding one or more samples. Such a container may be based on the design of polypropylene tubes or 96-well plates as presently used in many molecular biological applications. Ideally such a container will be adapted to receive at least one electrode component. That electrode component might, for example, be located as part of a lid for the container so that when it is used to close the container, the electrode component(s) reach into the sample solution. Conventional electrochemical cells are generally not regarded as disposable because of their relatively high cost. The use of disposable plastic ware has become standard practice in molecular biology because it mitigates the risks of sample contamination.

Certain illustrative embodiments of the invention will now be described in detail with reference to the accompanying drawings in which:

FIG. 19b shows baseline corrected data from FIG. 19a;

FIG. 20b shows baseline corrected data from FIG. 20a.

Figure 1:
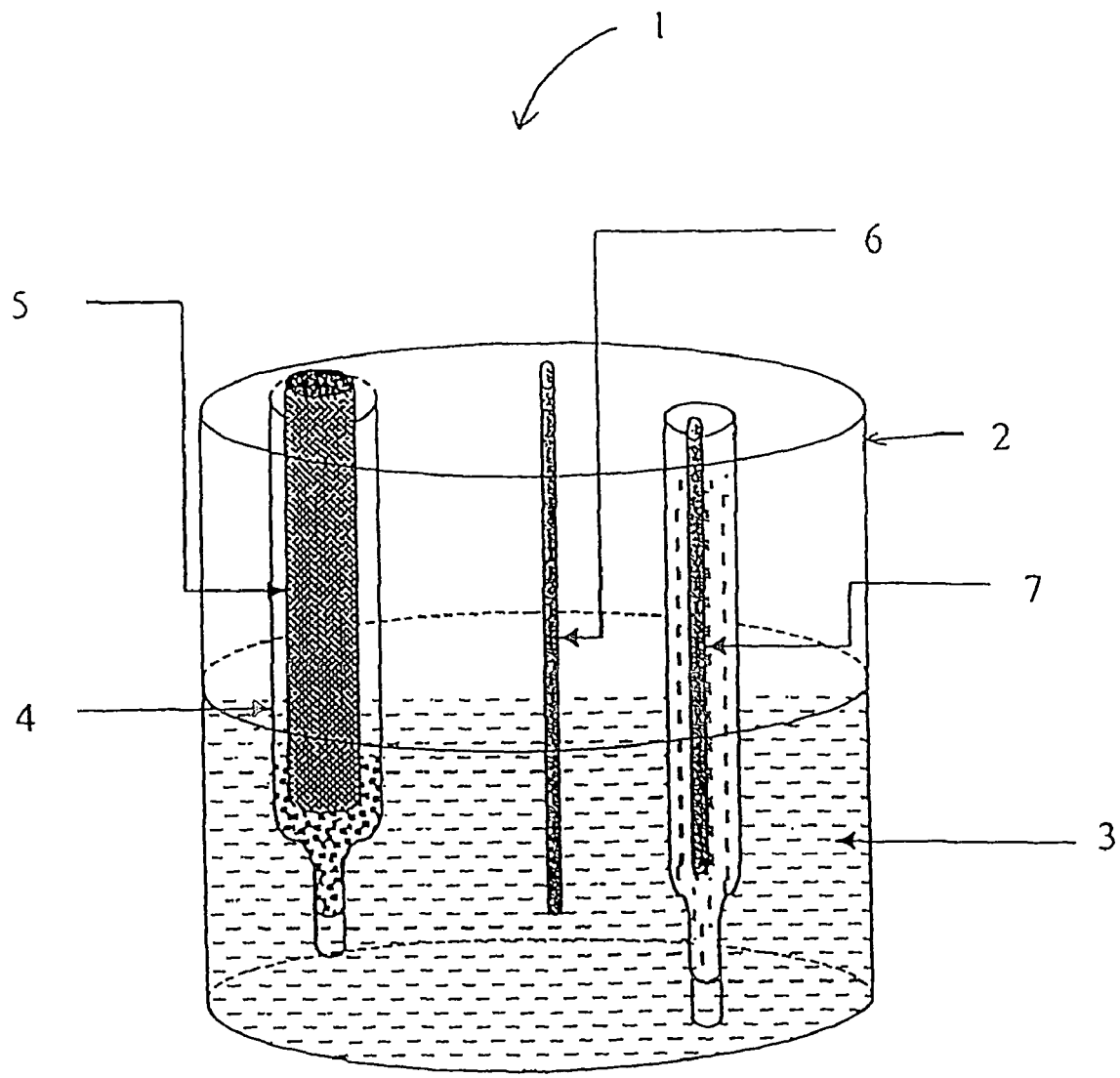
FIG. 1 is a schematic representation of an electrochemical cell used in differential pulse voltammetry measurements described herein.

With reference to FIG. 1, an electrochemical cell 1 suitable for use in the cyclic voltammetry experiments described herein comprises a vessel 2, containing a background electrolyte solution 3, which is an aqueous 100 mM solution of sodium chloride. Immersed in the solution 3 is a chamber 4, in which is located the sample to be tested and, immersed therein, a glassy carbon working electrode 5. A gold electrode may alternatively be used. Also immersed in the solution 3 is a counter-electrode 6 of platinum wire and a silver/silver chloride reference electrode 7 immersed in 4M potassium chloride solution, which solutions are in communication with others via a sintered disc.

The following Examples illustrate the invention:

Materials and Methods—Ferrocenylated BSA Preparations and Assays

Bovine serum albumin (lyophilised powder, approx. 99%), casein (bovine milk, purified powder), porcine pancreas trypsin (1120 BAEE units/mg solid), type II bovine pancreas α-chymotrypsin (51 units/mg solid), porcine stomach mucosa pepsin (632 units/mg solid), *Bacillus thermoproteolyticus rokko* thermolysin (44 units/mg solid), Tritirachium album proteinase K (33 units/mg solid), papaya latex papain (14 units/mg protein, 99%), type I-S soybean trypsin inhibitor, aminopeptidase (50 to 150 units/mg protein) and elastase (>=50 units/mg protein) were obtained from Sigma.

Ferrocene carboxylic acid was obtained from Aldrich Chemical Co.

Potassium bicarbonate (A.C.S. reagent), potassium carbonate (minimum 99%), and dimethyl sulfoxide (ACS reagent, min. 99.9%) were obtained from Sigma.

NAP 10 columns (G25 DNA grade SEPHADEX) were obtained from Amersham Biosciences. TRIZMA hydrochloride (99+%), TRIZMA base (99+%), sodium chloride (SIGMAULTRA min. 99.5%), sodium acetate (molecular biology grade), ethylenediaminetetraacetic acid tetrasodium salt (SIGMAULTRA min. 99.0%), sodium hydroxide (SIGMAULTRA min. 98%), DL-cystein hydrochloride (min. 98%), hydrochloric acid, and molecular biology grade water were obtained from Sigma. PONCEAU S (practical grade) ammonium persulfate (electrophoresis reagent), N,N,N',N'-tetramethyleneethylenediamine (TERMED), acrylamide/bis-acrylamide (37.5:1), 30% solution and EZ Blue gel staining reagent were obtained from Sigma. Acetic acid (glacial, 99.99+%) was obtained from Aldrich and isopropanol was obtained from Hayman. BIODYNE C membrane was obtained from Pall Life Sciences.

Incubations were performed using a PTC-100 Programmable Thermal Controller (MJ Research Inc.).

All solutions were prepared with autoclaved deionised water (WATERPRO system, Labconco). Materials and Methods-Electrochemical Detection The following were all obtained from BAS, Congleton, Cheshire UK:

Glassy carbon working electrode (catalogue number MF-2012)

Silver/silver chloride reference electrode (catalogue number MF-2079)

Platinum wire counter (auxiliary) electrode (catalogue number MW-4130)

Low volume cell (catalogue number MF-2040) comprising glass voltammetry vial and glass sample chamber, with replaceable vycor tip.

AUTOLAB electrochemical workstation (either PGSTAT30 with frequency response analyser or µAUTOLAB type II) obtained from Windsor Scientific, Slough, Berkshire.

EXAMPLE 1

Cyclic Voltammetry

This Example describes the cyclic voltammetry method used in Examples 5 to 11 below.

The low volume cell of FIG. 1 was filled with approximately 10 ml sodium chloride solution (100 mM). A 200 µl aliquot of the sample for analysis was placed in the glass sample chamber which was then placed in the low volume cell along with the reference and counter electrodes. The electrodes were connected to the AUTOLAB electrochemical workstation and differential pulse voltammetry carried out using the parameters described in Table 1. Prior to analysis the glassy carbon working electrode was polished (using BAS polishing kit catalogue number MF-2060) followed by conditioning. Electrode conditioning consists of cyclic voltammetry, sweeping between +−1 volt in the appropriate background buffer.

TABLE 1

| Parameters for differential pulse voltammetry: | |
|---|---|
| Parameter: | Anodic sweep |
| Conditioning potential (V) | 0 |
| Conditioning duration (s) | 10 |
| Deposition potential (V) | 0 |
| Deposition duration (s) | 0 |
| Equilibration time (s) | 0 |
| Modulation time (s) | 0.04 |
| Interval time (s) | 0.1 |
| Initial potential (V) | −0.1 |
| End potential (V) | 0.7 |
| Step potential (V) | 0.003 |
| Modulation amplitude (V) | 0.05 |

EXAMPLE 2

Synthesis of N-hydroxysuccinimide Ester of Ferrocenecarboxylic Acid

Ferrocenecarboxylic acid (303 mg, 1.32 mmol) and N-hydroxysuccinimide (170 mg, 1.47 mmol) were dissolved in dioxane (15 ml) and added with stirring to a solution of dicyclohexylcarbodiimide (305 mg, 1.48 mmol) in dioxane (3 ml). The mixture was stirred at room temperature for 24 hours during which time a precipitate was formed. The precipitate was removed by filtration, solvent was removed from the filtrate in vacuo and the resulting solid purified by silica gel column chromatography, eluting with 8:2 petrol:ethyl acetate. Yield 320 mg, 74%.

EXAMPLE 3a

Synthesis of Ferrocene Carbonyl Azide

Ferrocene carbonyl azide was prepared from ferrocenecarboxylic acid by reaction with oxalyl chloride and sodium azide.

EXAMPLE 3b

Synthesis of 4-(3'-ferrocenylureido)-1-benzoic acid

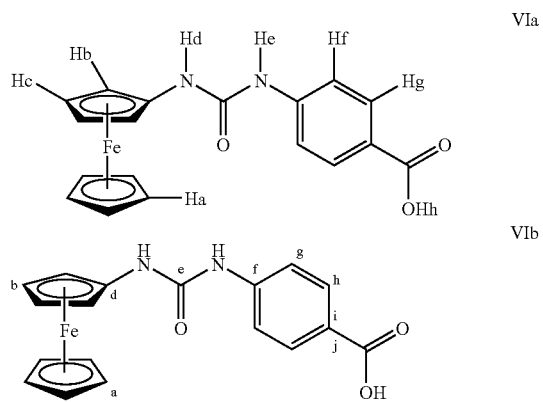

To a purged round-bottom flask was charged ferrocene carbonyl azide (300 mg, 1.18 mmol, 1.00 equiv.), 4-aminobenzoic acid (244 mg, 1.78 mmol, 1.50 equiv.) and 1,4-dioxane (40 ml) under nitrogen. The reaction mixture was stirred under nitrogen in a 100° C. bath for 2 hr 50 min and then allowed to cool to room temperature. 2M HCl (100 ml) was charged to the reaction mixture and the product was extracted into ethyl acetate (150 ml). This phase was washed with 2M HCl (100 ml), dried with sodium sulphate and concentrated in vacuo to afford the product. Further drying in a vacuum oven yielded as orange crystals (413 mg 96%). $^{1}$H-NMR δ (300 MHz, $d_6$-DMSO) 3.96 (2H, b, Hc), 4.14 (5H, s, Ha), 4.53 (2H, b, Hb), 7.54 (2H, m, Hf), 7.85 (2H, m, Hg), 7.98 (1H, s, Hd), 8.87 (1H, s, He) 12.57 (1H, s, Hh), where the position of each hydrogen is as shown in Formula Va. $^{13}$C-NMR δ (75.5 MHz, $d_6$-DMSO) 61.0 64.1 66.7 68.1 (Ca,d), 117.2 (Cg), 123.5 (Cj), 130.9 (Ch), 144.6 (Cf), 152.8 (Ce), where the position of each carbon is as shown in Formula VIb.

EXAMPLE 3c

Synthesis of N-hydroxysuccinimide ester of 4-(3'-ferrocenylureido)-1-benzoic acid Dicyclohexylcarbodiimide (DCC) (194 mg, 0.939 mmol, 1.14 equiv.) was dissolved in anhydrous 1,4-dioxane (2 ml) and charged to a purged round-bottom flask, under nitrogen. N-hydroxysuccinimide (108 mg, 0.939 mmol, 1.14 equiv.) was charged. 4-(3'-Ferrocenylureido)-1-benzoic acid (300 mg, 0.823 mmol 1.0 equiv.) was dissolved in anhydrous 1,4-dioxane (13 ml) and charged dropwise to the flask. The solution was stirred at room temperature for 23 hr. A small amount of light brown solid was removed from the red/orange reaction mixture by Buchner filtration. Water (100 ml) and ethyl acetate (50 ml) were charged to the reaction mixture. The ethyl acetate phase was separated and the aqueous was extracted with ethyl acetate (100 ml). The ethyl acetate phases were combined, dried with sodium sulphate and concentrated in vacuo to afford the crude product as an orange oil, which was purified using silica flash chromatography with a gradient system from ethyl acetate 60/petroleum ether (bp 40-60° C.) 40 to ethyl acetate. Drying in a vacuum oven yielded N-hydroxysuccinimide ester of 4-(3'-ferrocenylureido)-1-benzoic acid as fine orange crystals (237 mg, 66%). $R_f$ (5:1 ethyl acetate/petroleum ether (bp 40-60° C.)=0.41 $^1$H-NMR δ (300 MHz, $d_6$-DMSO) 2.88 (4H, s, Hh), 3.98 (2H, t, J=1.8 Hz, Hc), 4.16 (5H, s, Ha), 4.55 (2H, t, J=1.8 Hz, Hb), 7.68 (2H, m, Hf), 8.00 (2H, m, Hg), 8.11 (1H, s, Hd), 9.16 (1H, s, He). $^{13}$C-NMR δ (75.5 MHz, $d_6$-DMSO) 25.9 (Cl), 61.1 64.2 (Cb and Cc), 69.1 (Ca), 117.7 (Cg), 131.9 (Ch), 170.9 (Ck). MS (FAB+m/z) 462.07 [M+H].

EXAMPLE 4a

Synthesis of Ferrocenylated Proteins

The following nomenclature is adopted herein:

| | |
|---|---|
| Fc = | ferrocene methanoyl group, such that Fc-OH is ferrocene carboxylic acid and Fc-NHR is a ferrocene methyl amido compound. |
| FcU = | 4-(3'-ferrocenylureido)-1-benzoyl group, such that FcU-OH 4-(3'-ferrocenylureido)-1-benzoic acid and FcU-NHR is a 4-(3'-ferrocenylureido)-1-benzamide compound. |
| BSA = | Bovine serum albumin |

The same general procedure was used for the synthesis of all of the ferrocene labelled proteins. The synthesis of Fc-BSA is described by way of example.

Lyophilised BSA was resuspended in the correct volume of $K_2CO_3$/$KHCO_3$ buffer (200 mM, pH 8.5) to give a BSA concentration of 10 mgml$^{-1}$. BSA solution (100 μl, 10 mgml$^{-1}$) was added slowly with vortexing to a solution of the N-hydroxysuccinimide ester of ferrocenecarboxylic acid in DMSO (100 μl, 375 mM). The solution was shaken at room temperature for 2 hours, it was then diluted with tris HCl (800 μl, 100 mM, pH 7.8) and purified using two NAP 10 columns (following the protocol supplied), eluting with firstly with tris HCl (800 μl, 100 mM, pH 7.8), secondly with deionised water.

BSA concentration was determined by blotting onto BIO-DYNE C membrane using BSA standard concentrations and staining with PONCEAU S. Using the method, BSA concentrations were found to be 0.3-0.6 mgml$^{-1}$. Presence of the ferrocene label was confirmed by voltammetric analysis.

FcU-labelled proteins were prepared in an analogous fashion.

Figure 2:
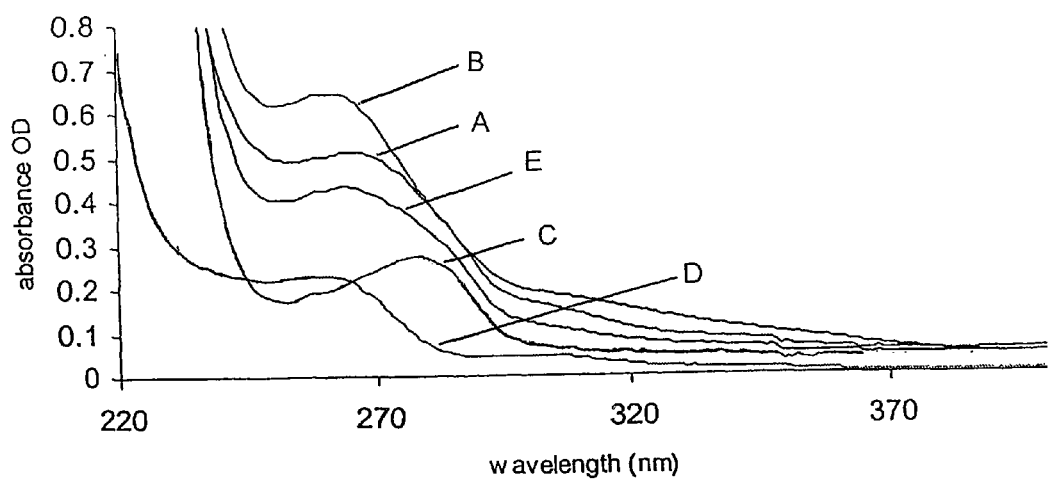
FIG. 2 is a set of overlaid UV-visible spectra for ferrocene and BSA conjugates and mixtures.

The average number of ferrocene groups present on each labelled BSA molecule was analysed by UV-visible spectroscopy. The UV-visible spectrum of the Fc-BSA conjugate obtained by the procedure described above was compared with the spectra of Fc/BSA mixtures at various ratios. The overlaid spectra are shown in FIG. 2 in which line A is the spectrum for the sample; line B is for BSA:Fc-OH Acid 20:1; line C is for BSA alone; line D is for Fc-OH alone and line E is for BSA:Fc-OH 10:1. From those data, the number of ferrocene molecules present per BSA molecule is estimated to be between 10 and 20.

EXAMPLE 4b

Synthesis of Ferrocenylated Alanine (Fc-Ala, Formula IIIa)

Two equivalents of EDCL (1-[3-(Dimethylamino)propyl] 3-ethylcarbodimmidehydrochloride) were added to a vigorously stirring suspension of ferrocenemethylamine and Boc-Ala-OH(N-Boc-alanine) with 2.1 equivalents of DMAP (4-(N,N-dimethylamino)pyridine) in dry DCM (dichloromethane) under $N_2$. The reaction was stirred overnight. The reaction was then diluted with DCM and poured into 1N HCL. The layers were separated and the organic layer dried with $MgSO_4$, filtered and the solvent removed.

EXAMPLE 4c

Synthesis of Ferrocenylated Trialanine Peptide (Fc-Ala-Ala-Ala, Formula IIIb)

The Ac-Ala-Ala-Ala-OH was obtained from Sigma-Aldrich

Two equivalents of EDCL(1-[3-(Dimethylaminopropl]-3-ethylcarbodiimide hydrochloride) were added vigorously stirring suspension of ferrocenemethylamine and Ac-Ala-Ala-Ala-OH (trialanine with acetylation of terminal amino group) with 2.1 equivalents of DMAP(4-NN-dimethylformamide) under $N_2$. The reaction was stirred overnight. Methanol was then added and the product was precipitated using $CHCl_3$ and was obtained by centrifuge, decanting the supernatant and washing with further $CHCl_3$. No deprotection of the acetylated terminal amino group was carried out.

EXAMPLE 5

Protease Assays

Protease assays were performed as follows unless stated otherwise. Lyophilised enzymes were re-suspended to give a concentration of 10 mgml$^{-1}$. Enzymes were resuspended in the following solutions: HCl (1 mM, pH 3.0) (trypsin, α-chymotrypsin, pepsin), NaCl (100 mM) (proteinase K, elastase, papain, carboxypeptidase, thermolysin). 75 μl of Fc-BSA solution (0.3-0.6 mgml$^{-1}$) was used per reaction. Each reaction was carried out in a total volume of 200 μl and the reactions were performed in the following buffers (final concentrations are given): 100 mM tris HCl pH7.8 (trypsin, α-chymotrypsin, thermolysin, proteinase K); 100 mM tris HCl pH 8.5 (elastase); 200 mM sodium acetate, 200 mM cysteine, 20 mM EDTA (papain); 10 mM HCl pH 2.0 (pepsin); 25 mM tris HCl pH7.5, 500 mM NaCl (carboxypeptidase). 2 μl enzyme (10 mgml$^{-1}$) was added to the 2001 reaction mixture. Samples were incubated at 37° C. for 1 hour. The reaction products were analysed by differential pulse voltammetry as described in Example 1.

Data Presentation

Baseline corrected data is displayed as overlayed files in addition to the raw data. Baseline corrected data was obtained using GPES MANAGER (Ecochemie BV, Utrecht, Netherlands) selecting baseline correction from the edit data menu, selecting moving average, minimum peak width 0.003V.

EXAMPLE 5A

Digestion of Fc-BSA with Trypsin

Figure 3A:
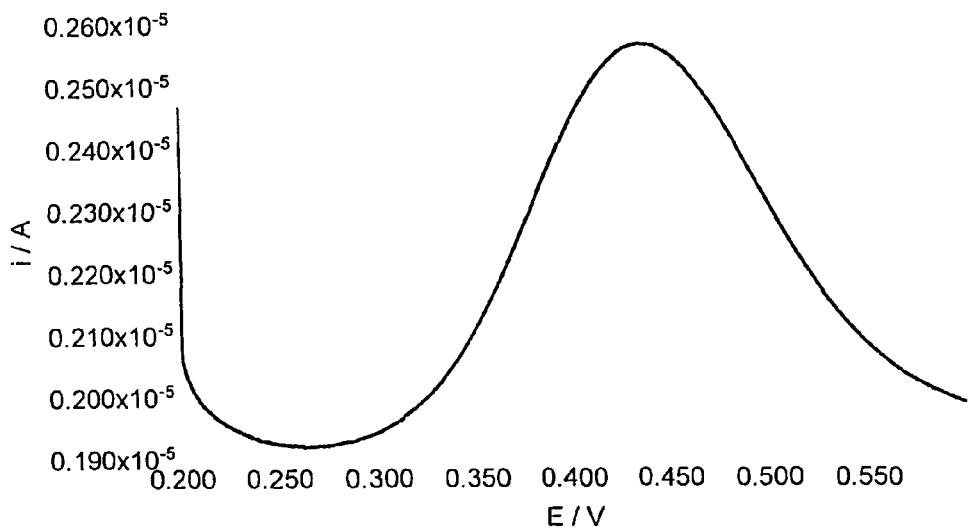
FIGS. 3a, 3b and 3c are differential pulse voltammograms of trypsin digestion products of Fc-BSA as described in Example 5A.
Figure 3B:
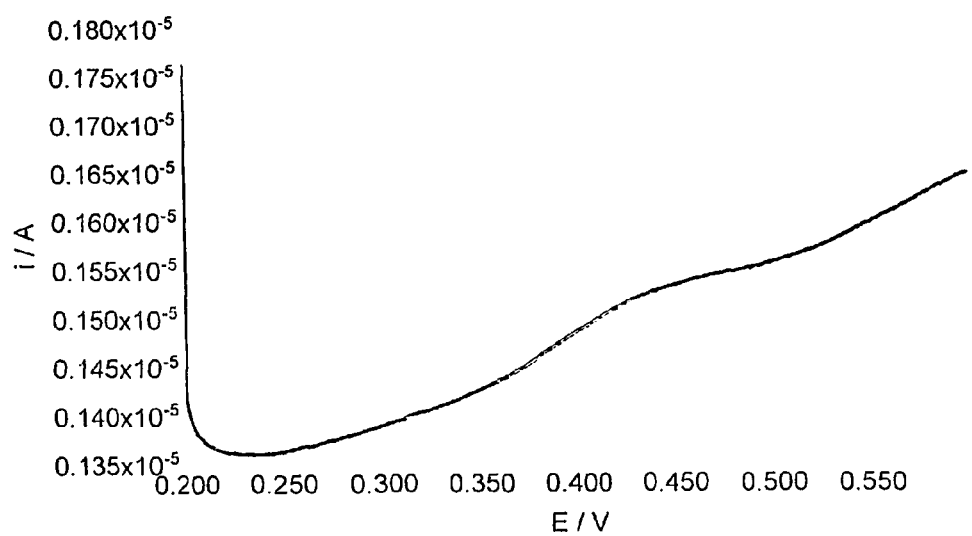
Figure 3C:
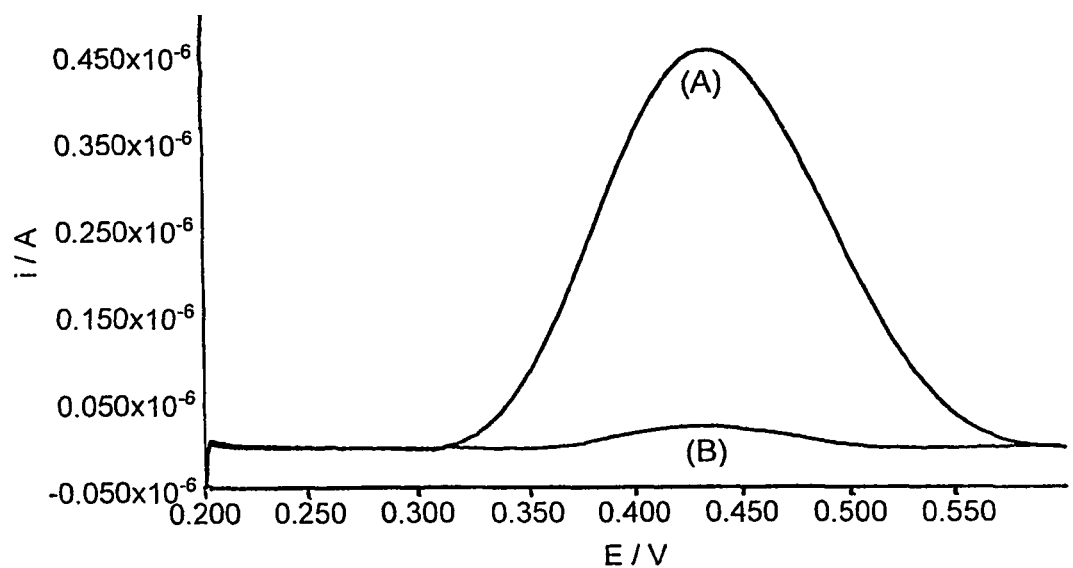

A digestion of Fc-BSA with trypsin was carried out as described above. The differential pulse voltammogram results are shown in FIG. 3 in which (a) is the trace for the digested product; (b) is the trace for the product of a no-trypsin control and (c) shows the data from (a) and (b) with baseline correction. The positive reaction has a peak position of 435 mV and a peak height of $4.58\times10^{-7}$ A; the no trypsin control reaction has a peak position of 432 mV and a peak height of $2.55\times10^{-8}$ A.

As is seen in FIG. 3, the current observed at 435 mV increases by a factor of 18 upon digestion of the protein to which the electrochemical marker is attached.

EXAMPLE 5B

Digestion of Fc-BSA with α-chymotrypsin

Figure 4A:
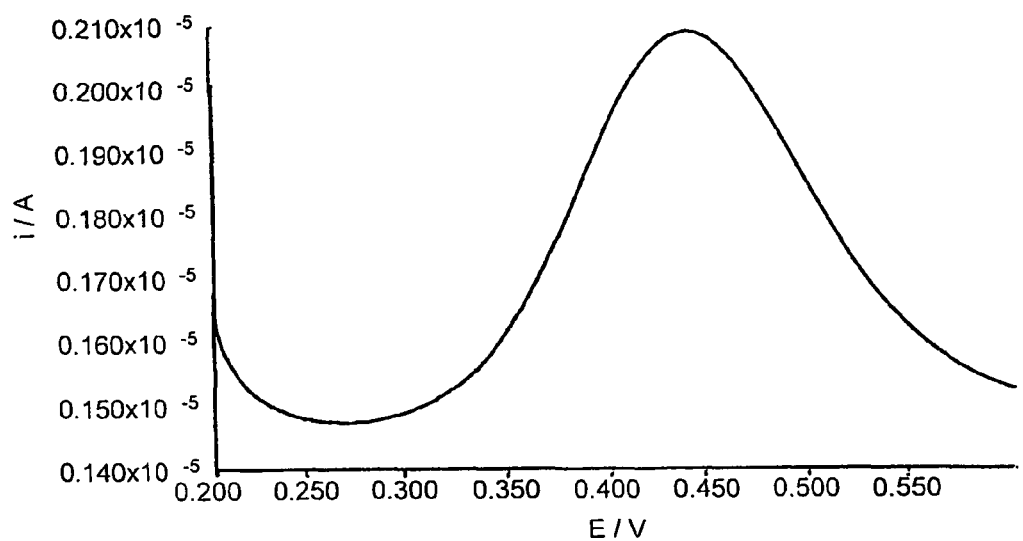
FIGS. 4a, 4b and 4c are differential pulse voltammograms of α-chymotrypsin digestion products of Fc-BSA as described in Example 5B.
Figure 4B:
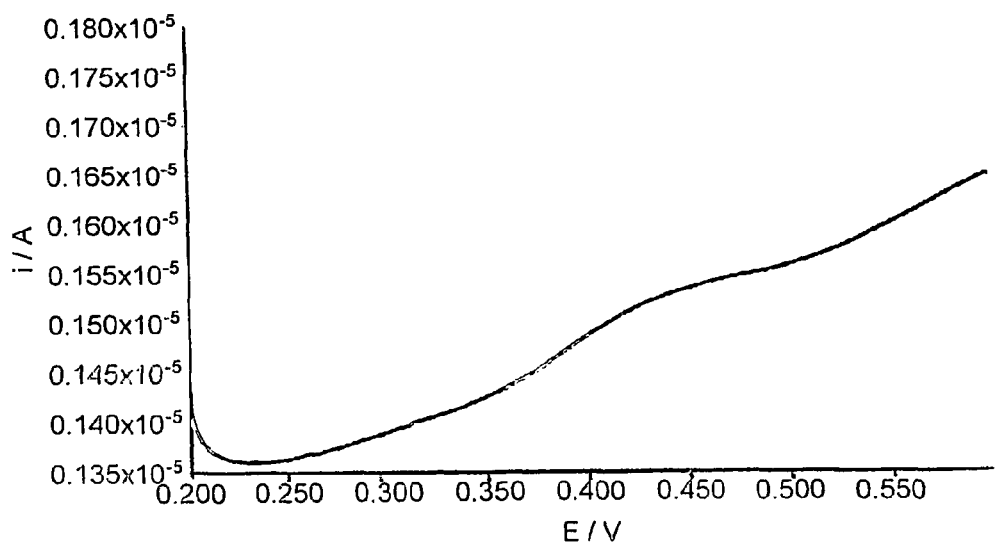
Figure 4C:
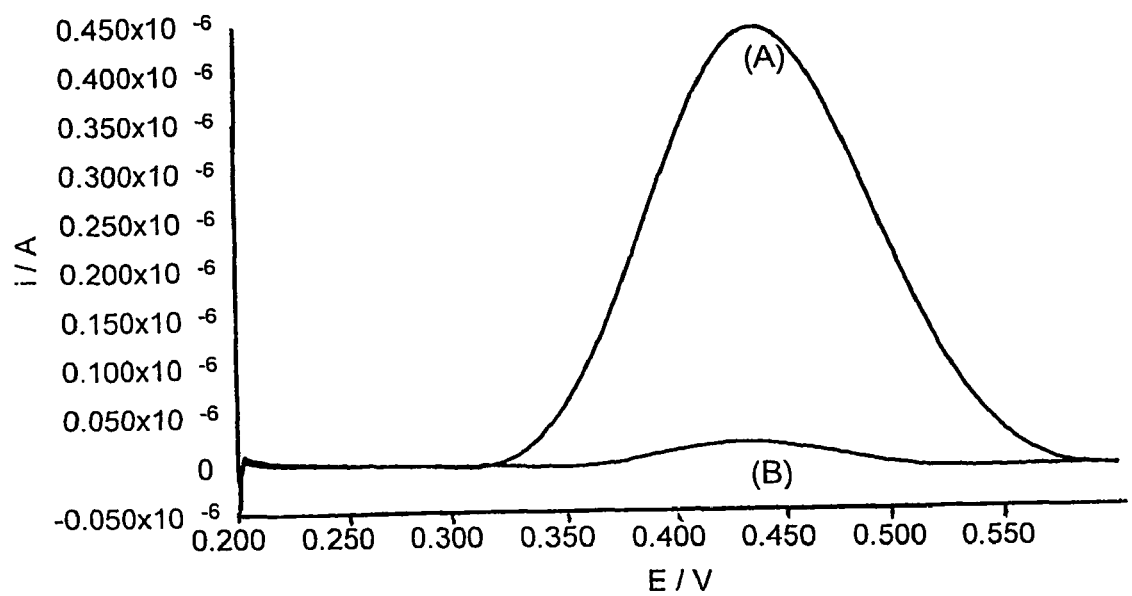

A digestion of Fc-BSA with α-chymotrypsin was carried out as described above. The differential pulse voltammogram results are shown in FIG. 4 in which (a) is the trace for the digested product; (b) is the trace for the product of a no-α-chymotrypsin control and (c) shows the data from (a) and (b) with baseline correction. The positive reaction has a peak position of 438 mV and a peak height of $4.48\times10^{-7}$ A; the no α-chymotrypsin control reaction has a peak position of 432 mV and a peak height of $2.55\times10^{-8}$ A.

EXAMPLE 5C

Digestion of Fc-BSA with Elastase

Figure 5A:
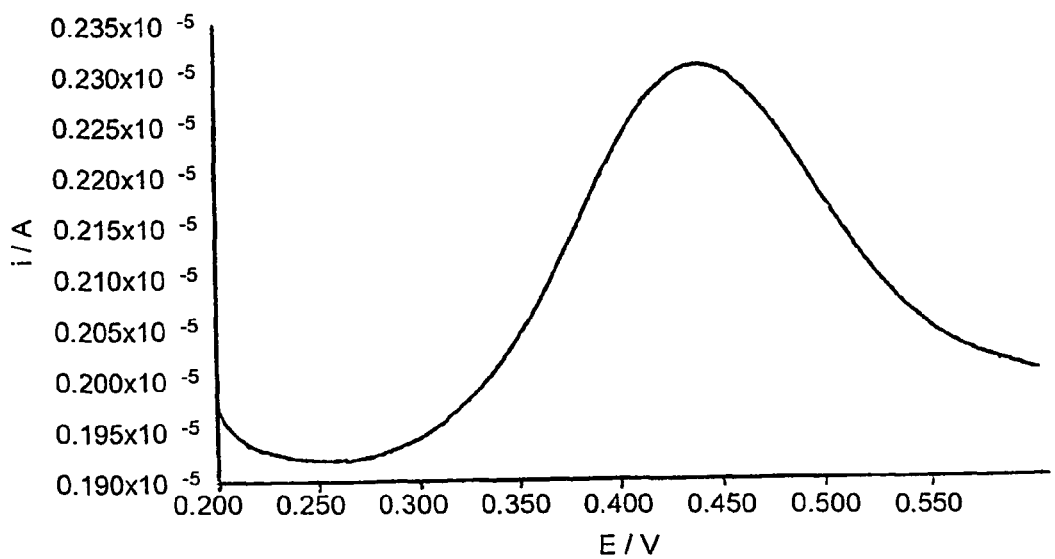
FIGS. 5a, 5b and 5c are differential pulse voltammograms of elastase digestion products of Fc-BSA as described in Example 5C.
Figure 5B:
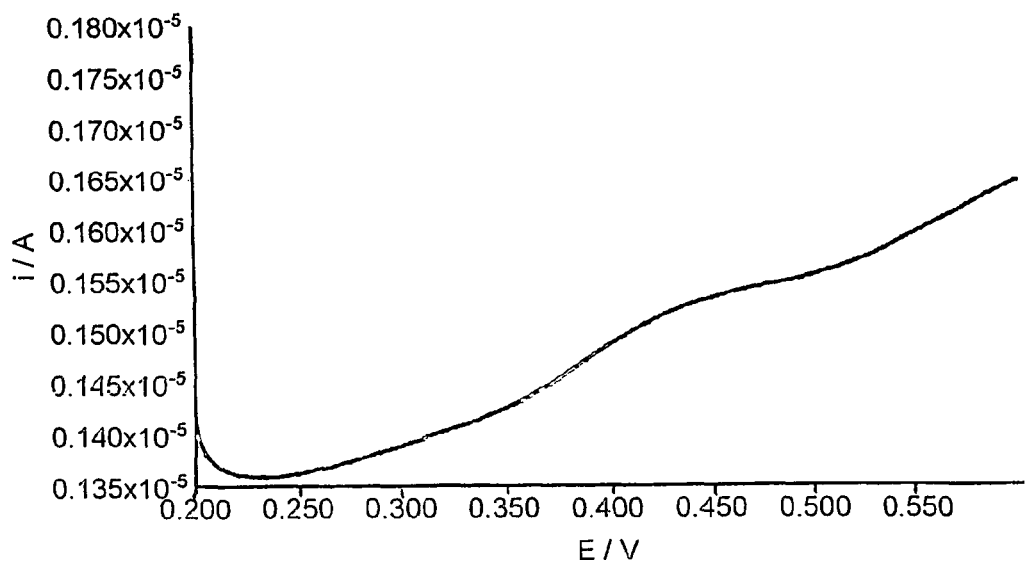
Figure 5C:
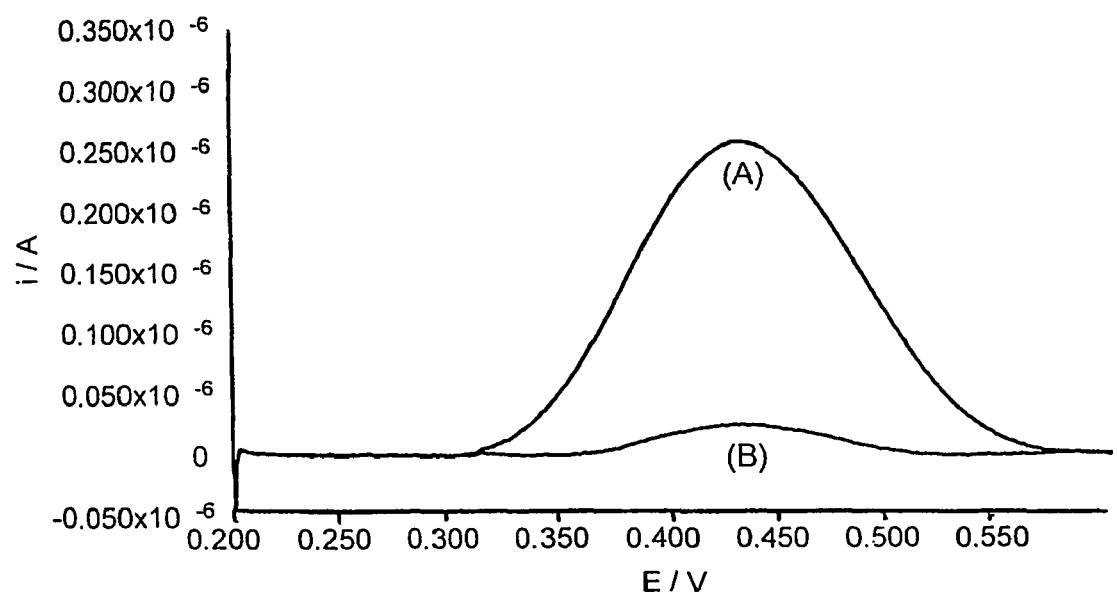

A digestion of Fc-BSA with elastase was carried out as described above. The differential pulse voltammogram results are shown in FIG. 5 in which (a) is the trace for the digested product; (b) is the trace for the product of a no-elastase control and (c) shows the data from (a) and (b) with baseline correction. The positive reaction has a peak position of 430 mV and a peak height of $2.57\times10^{-7}$ A; the no elastase control reaction has a peak position of 432 mV and a peak height of $2.55\times10^{-8}$ A.

EXAMPLE 5D

Digestion of Fc-BSA with Pepsin

Figure 6A:
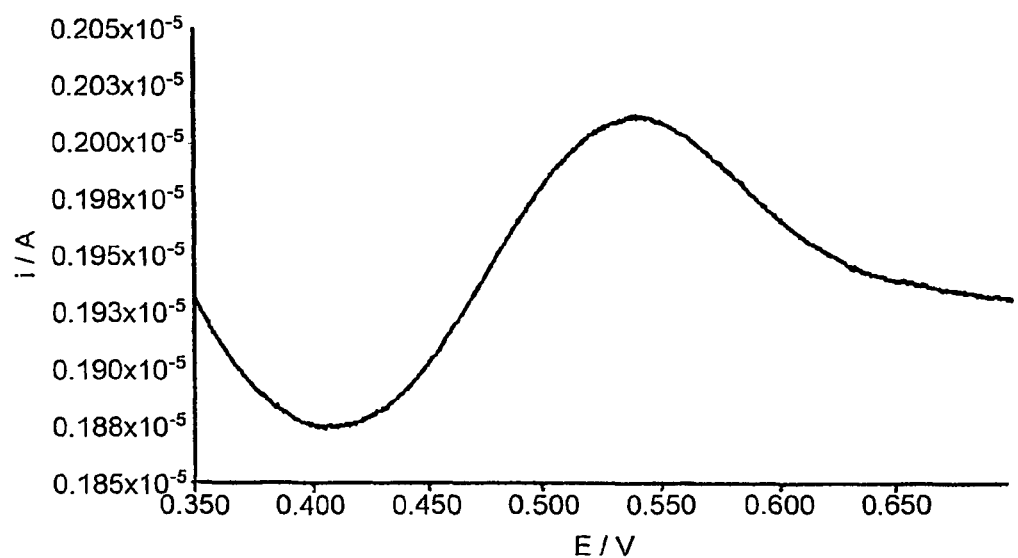
FIGS. 6a, 6b and 6c are differential pulse voltammograms of pepsin digestion products of Fc-BSA as described in Example 5D.
Figure 6B:
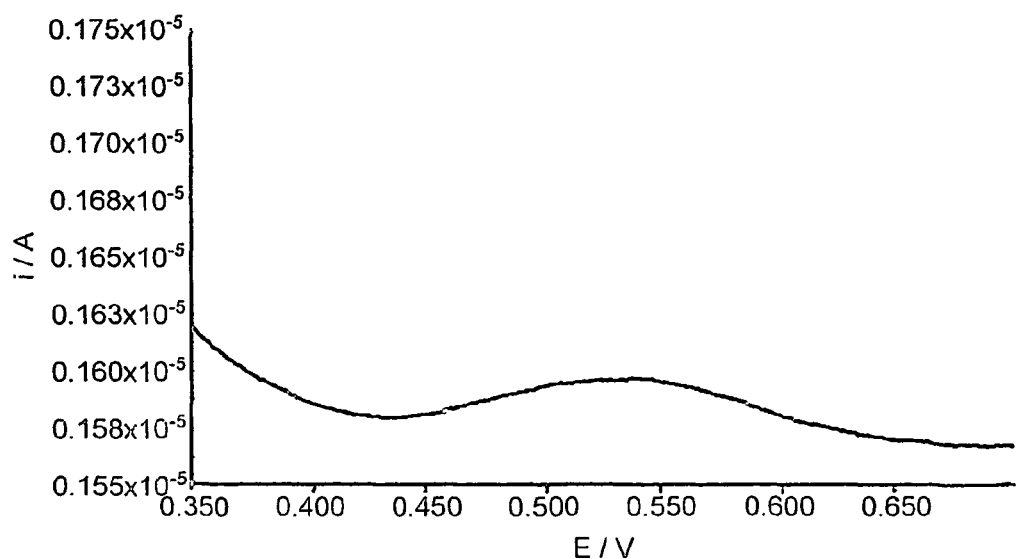
Figure 6C:
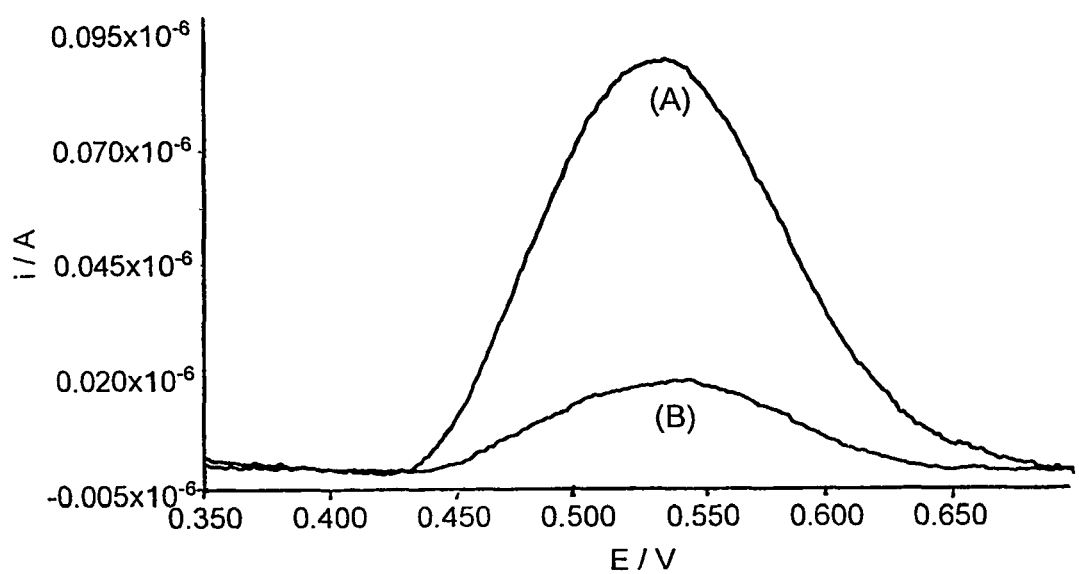

A digestion of Fc-BSA with pepsin was carried out as described above. The differential pulse voltammogram results are shown in FIG. 6 in which (a) is the trace for the digested product; (b) is the trace for the product of a no-pepsin control and (c) shows the data from (a) and (b) with baseline correction. The positive reaction has a peak position of 537 mV and a peak height of $8.90\times10^{-8}$ A; the no-pepsin control reaction has a peak position of 522 mV and a peak height of $4.19\times10^{-8}$ A.

EXAMPLE 5E

Digestion of Fc-BSA with Carboxypeptidase

Figure 7A:
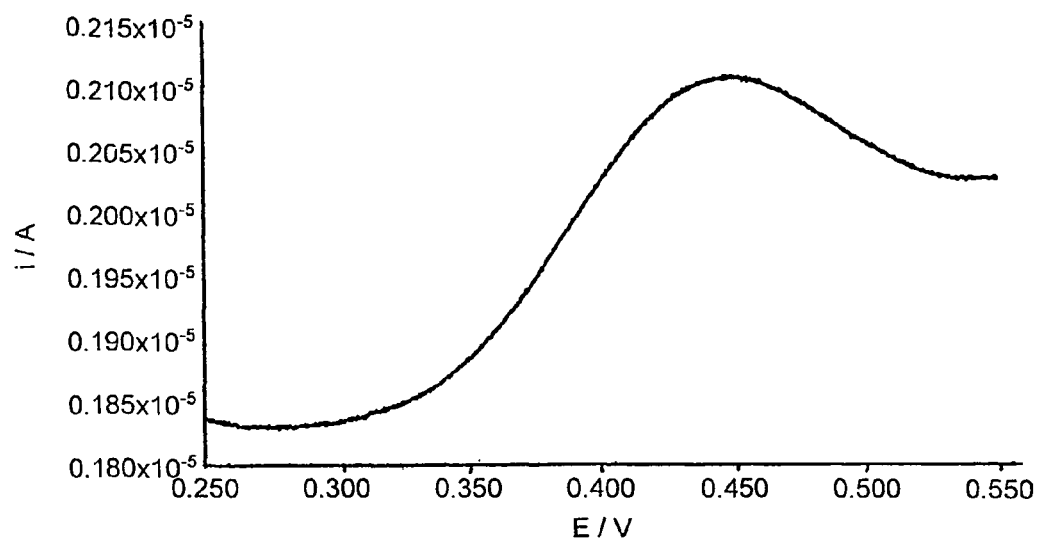
FIGS. 7a, 7b and 7c are differential pulse voltammograms of carboxypeptidase digestion products of Fc-BSA as described in Example 5E.
Figure 7B:
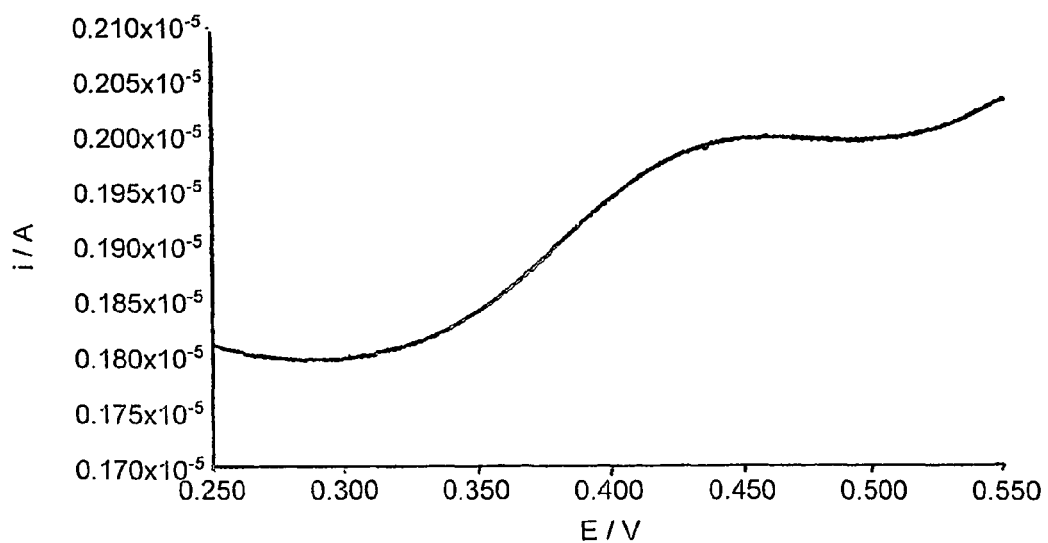
Figure 7C:
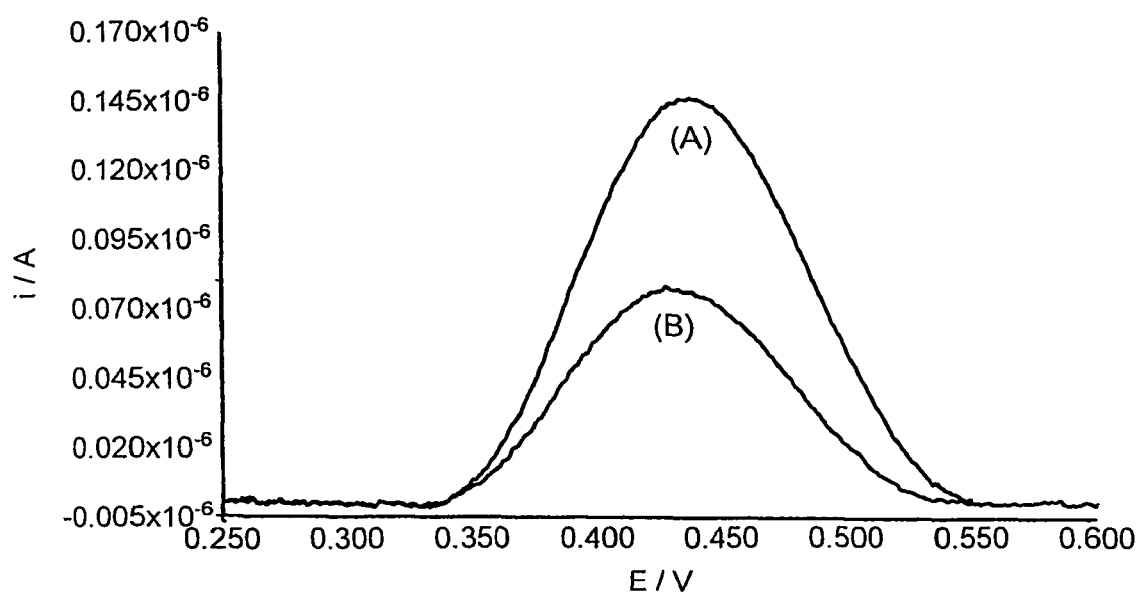

A digestion of Fc-BSA with carboxypeptidase was carried out as described above. The differential pulse voltammogram results are shown in FIG. 7 in which (a) is the trace for the digested product; (b) is the trace for the product of a no-carboxypeptidase control and (c) shows the data from (a) and (b) with baseline correction. The positive reaction has a peak position of 435 mV and a peak height of $1.31\times10^{-7}$ A; the no elastase control reaction has a peak position of 427 mV and a peak height of $6.86\times10^{-8}$ A.

EXAMPLE 5F

Digestion of Fc-BSA with Thermolysin at 37° C.

Figure 8A:
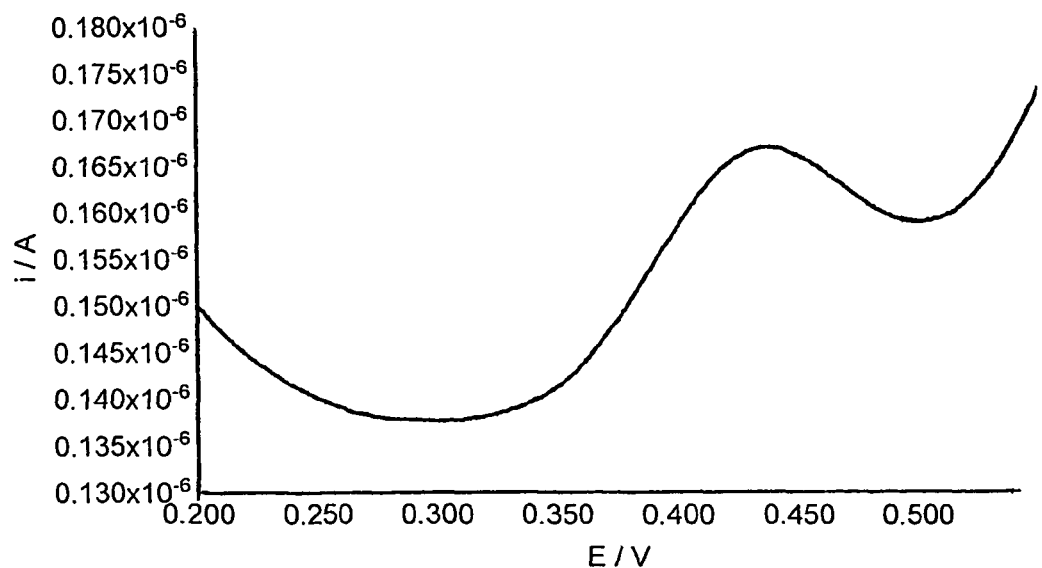
FIGS. 8a, 8b and 8c are differential pulse voltammograms of thermolysin digestion products (at 37° C.) of Fc-BSA as described in Example 5F.
Figure 8B:
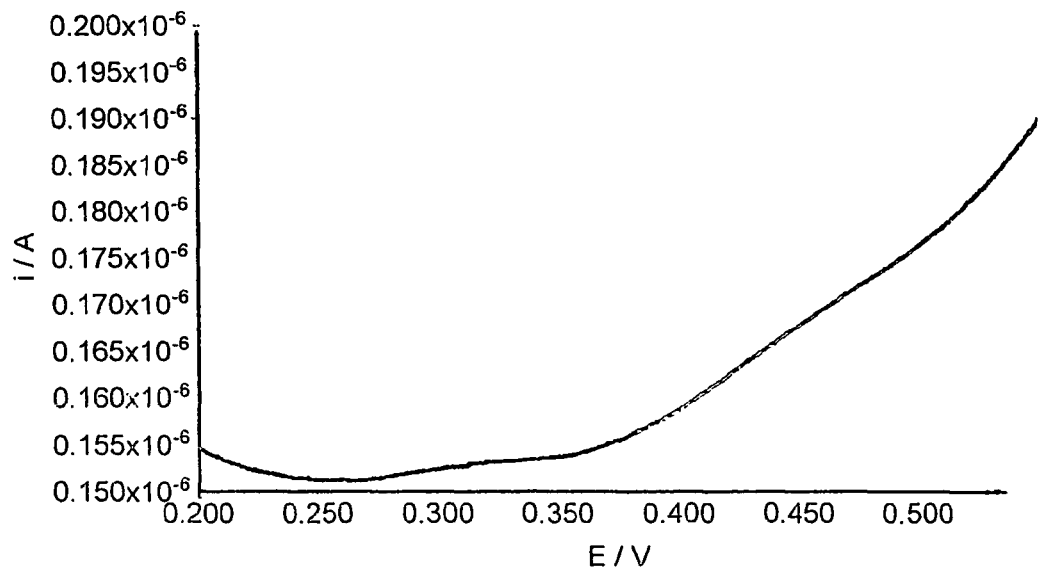
Figure 8C:
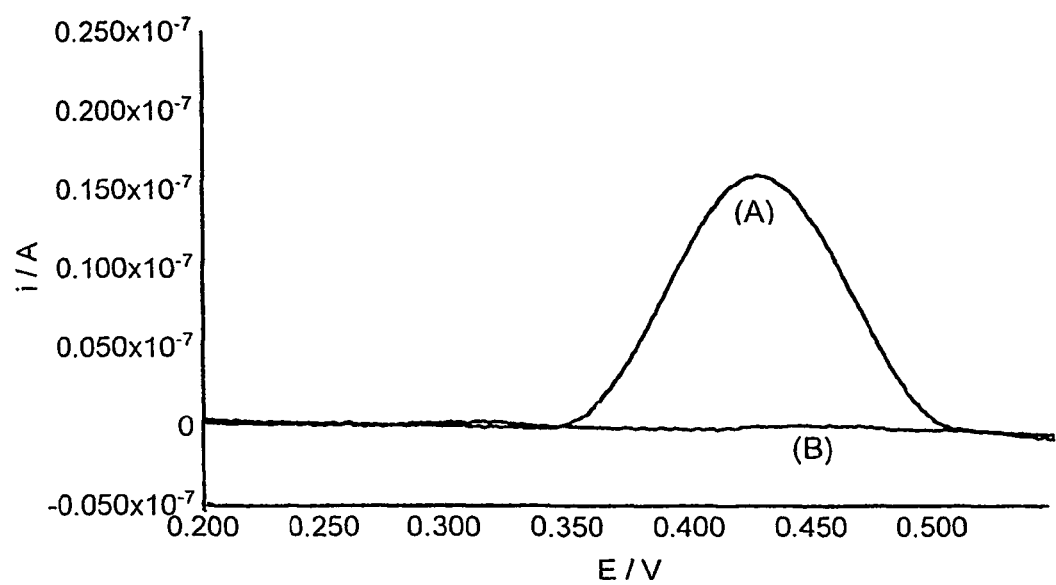

A digestion of Fc-BSA with thermolysin was carried out as described above with the digestion incubation at 37° C. The differential pulse voltammogram results are shown in FIG. 8 in which (a) is the trace for the digested product; (b) is the trace for the product of a no-thermolysin control and (c) shows the data from (a) and (b) with baseline correction. The positive reaction has a peak position of 429 mV and a peak height of $1.62\times10^{-8}$ A; no peak was found in the no-thermolysin control reaction.

EXAMPLE 5G

Digestion of Fc-BSA with Thermolysin at 70° C.

Figure 9A:
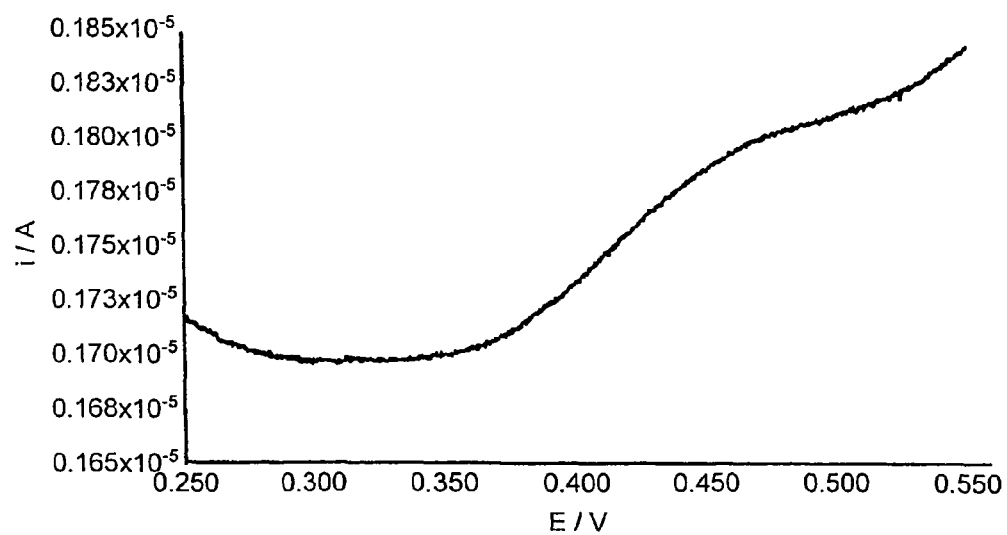
FIGS. 9a, 9b and 9c are differential pulse voltammograms of thermolysin digestion products (at 70° C.) of Fc-BSA as described in Example 5G.
Figure 9B:
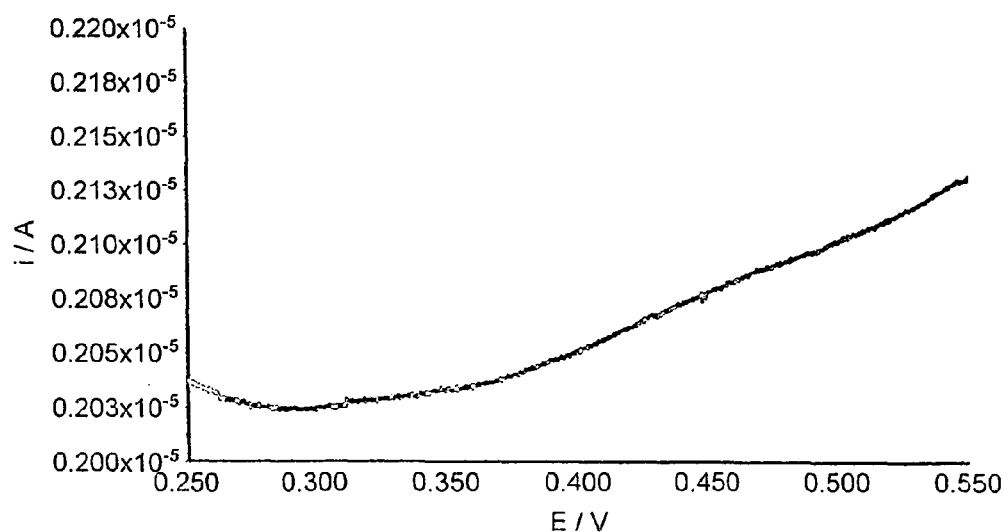
Figure 9C:
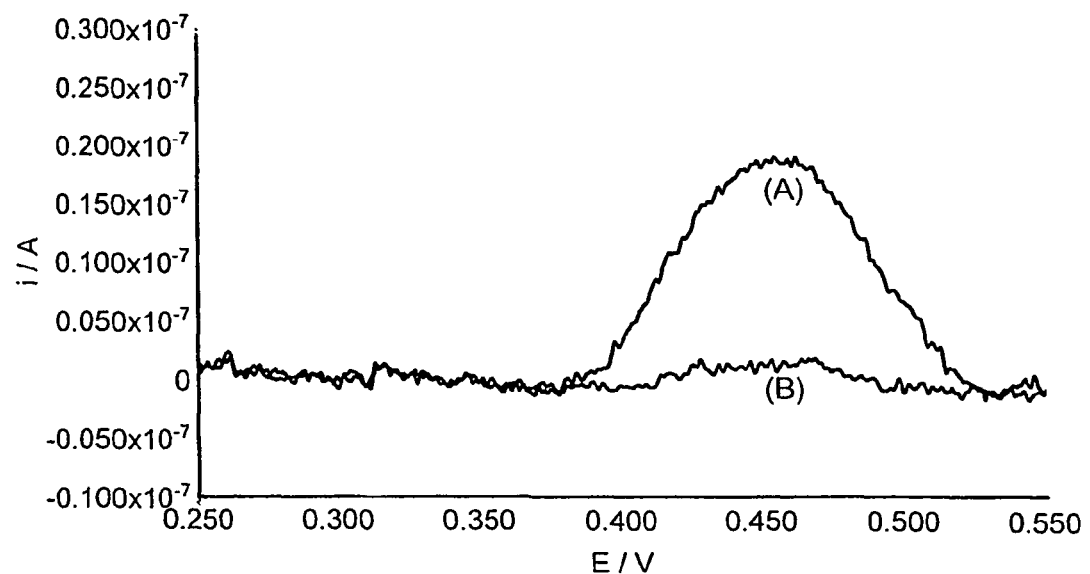

A digestion of Fc-BSA with thermolysin was carried out as described above with the digestion incubation at 70° C. The differential pulse voltammogram results are shown in FIG. 9 in which (a) is the trace for the digested product; (b) is the trace for the product of a no-thermolysin control and (c) shows the data from (a) and (b) with baseline correction. The positive reaction has a peak position of 455 mV and a peak height of $2.0\times10^{-8}$ A; no peak was found in the no-thermolysin control reaction.

EXAMPLE 5H

Digestion of BSA with Trypsin

Figure 10A:
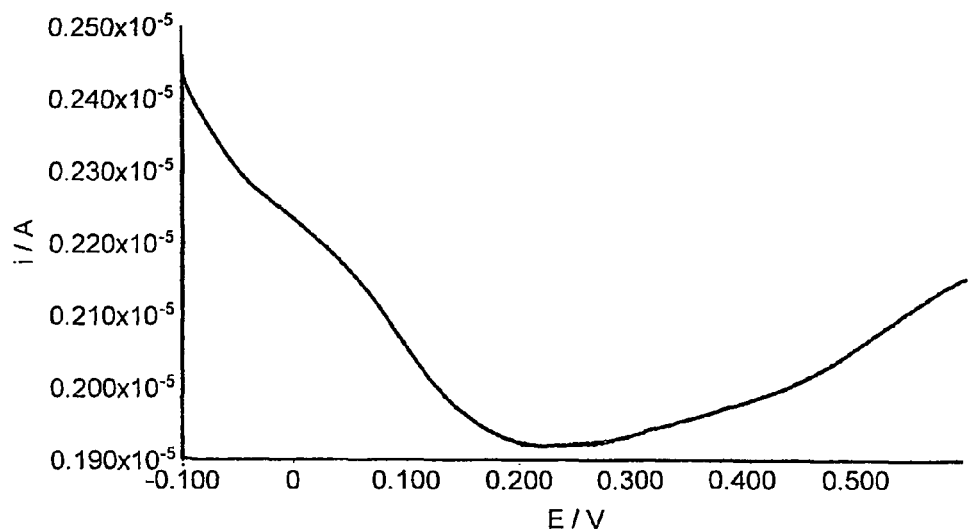
FIGS. 10a and 10b are differential pulse voltammograms of trypsin digestion products of unlabelled BSA as described in Example 5H.
Figure 10B:
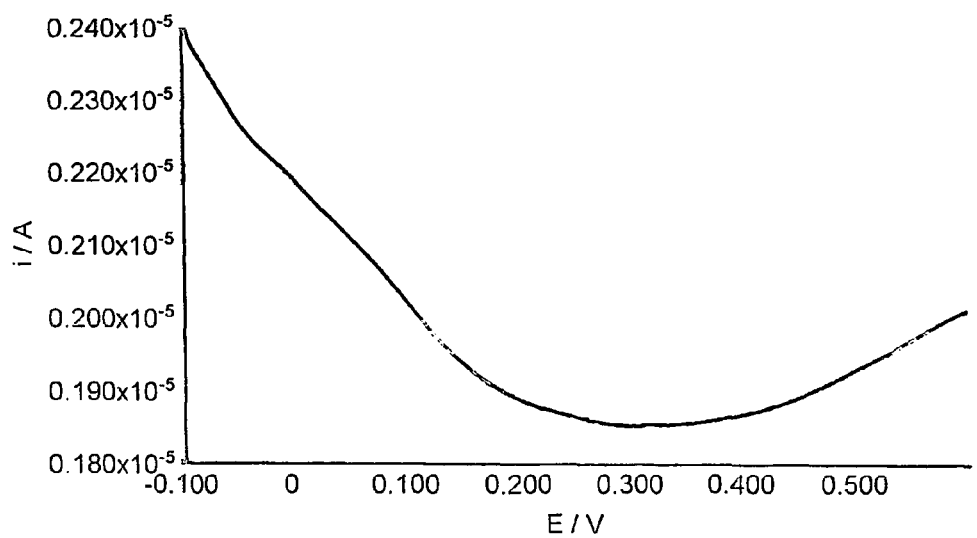

A digestion of unlabelled BSA with trypsin was carried out in the same manner as for the labelled molecules as described above. The differential pulse voltammogram results are shown in FIG. 10 in which (a) is the trace for a no-trypsin control reaction and (b) is the trace for trypsin BSA reaction. No peaks were found in either reaction product solution.

EXAMPLE 5I

Digestion of FcU-BSA with Trypsin

Figure 11A:
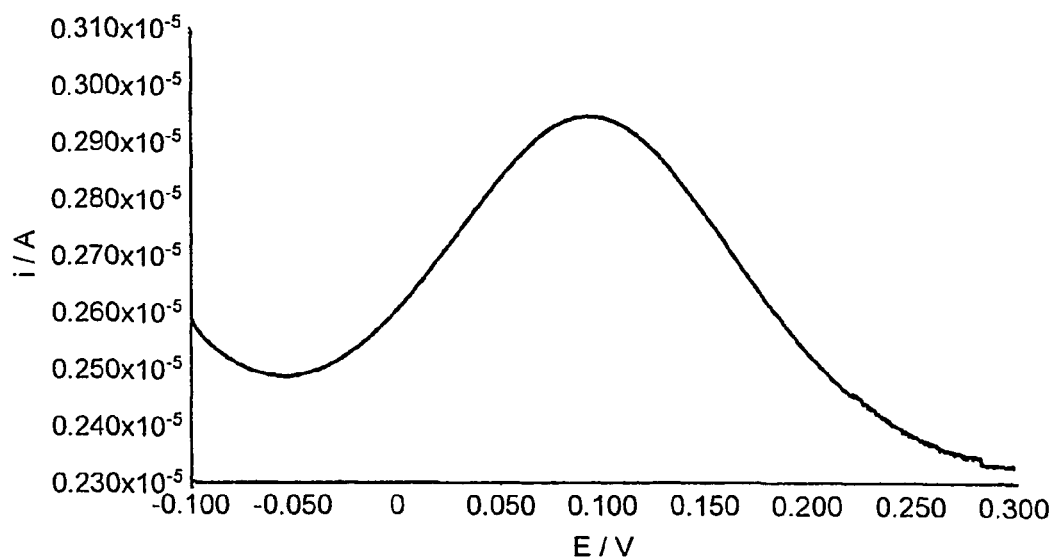
FIGS. 11a, 11b and 11c are differential pulse voltammograms of trypsin digestion products of FcU-BSA as described in Example 5I.
Figure 11B:
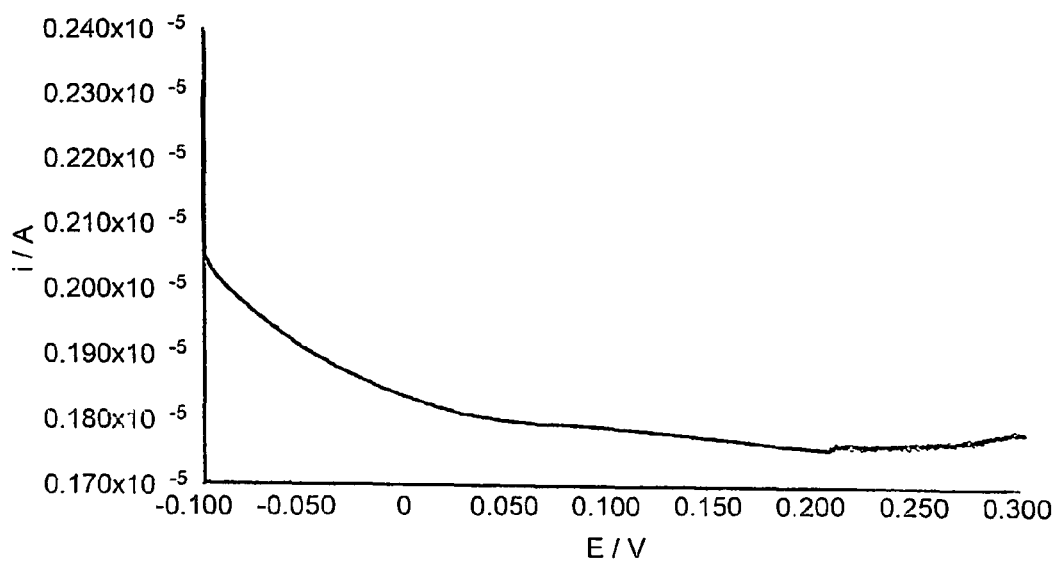
Figure 11C:
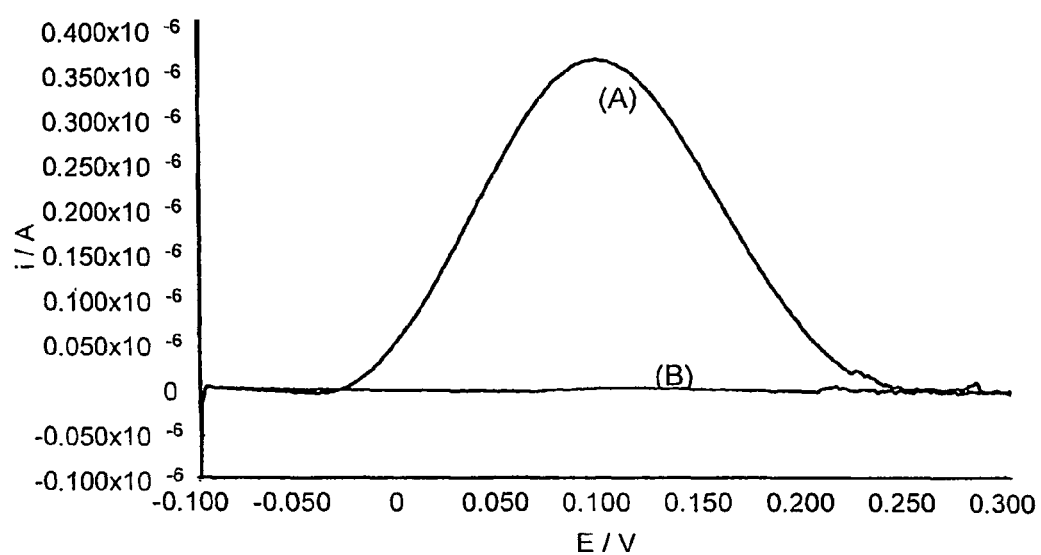

A digestion of FcU-BSA with trypsin was carried out as described above. The differential pulse voltammogram results are shown in FIG. 11 in which (a) is the trace for the digested product; (b) is the trace for the product of a no-trypsin control and (c) shows the data from (a) and (b) with baseline correction. The positive reaction has a peak position of 97 mV and a peak height of $5.01\times10^{-7}$ A; there was no peak in the no-trypsin control reaction.

EXAMPLE 5J

Digestion of FcU-BSA with Papain

Figure 12A:
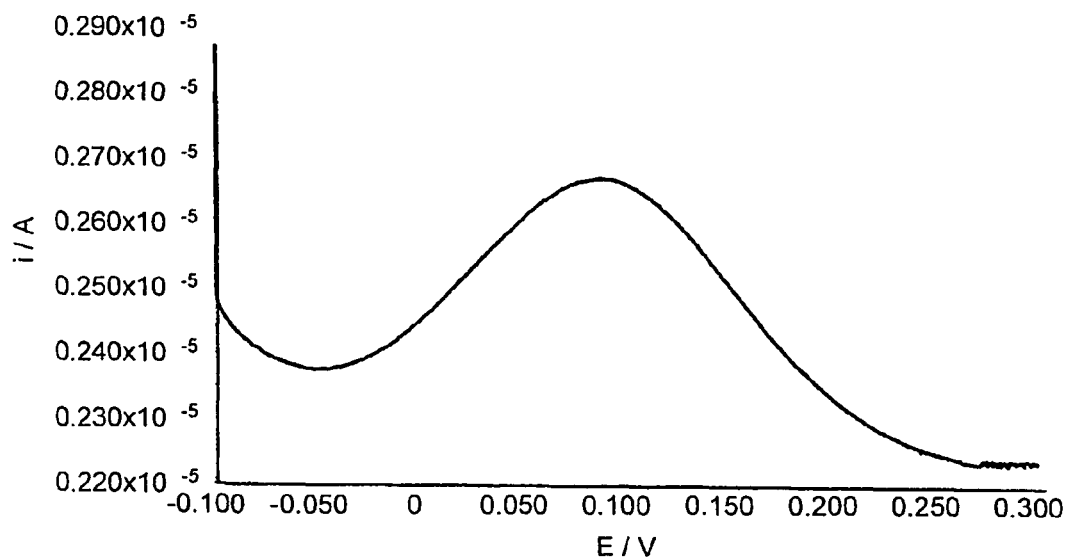
FIGS. 12a, 12b and 12c are differential pulse voltammograms of papain digestion products of FcU-BSA as described in Example 5J.
Figure 12B:
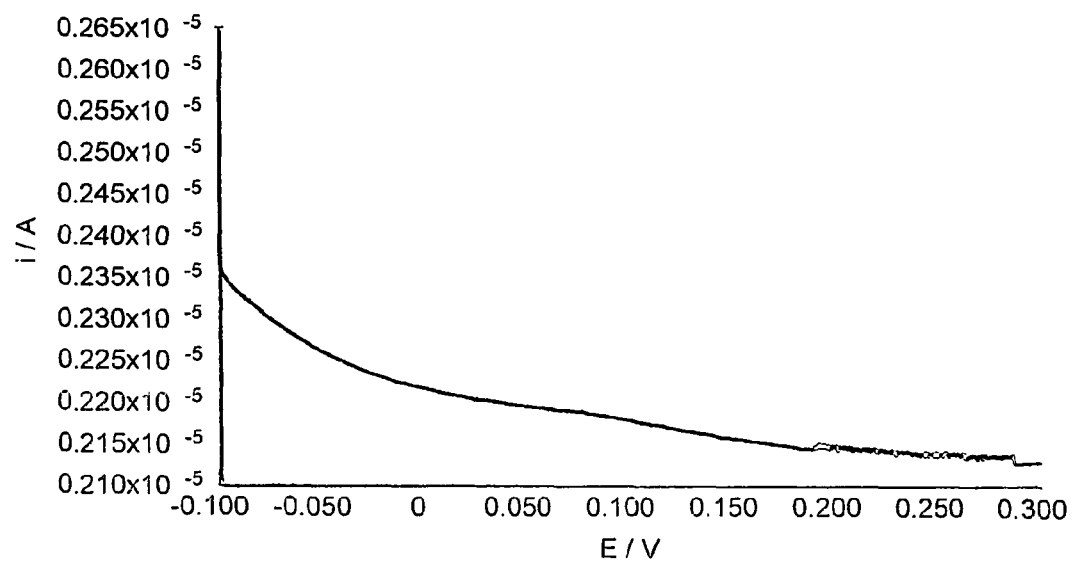
Figure 12C:
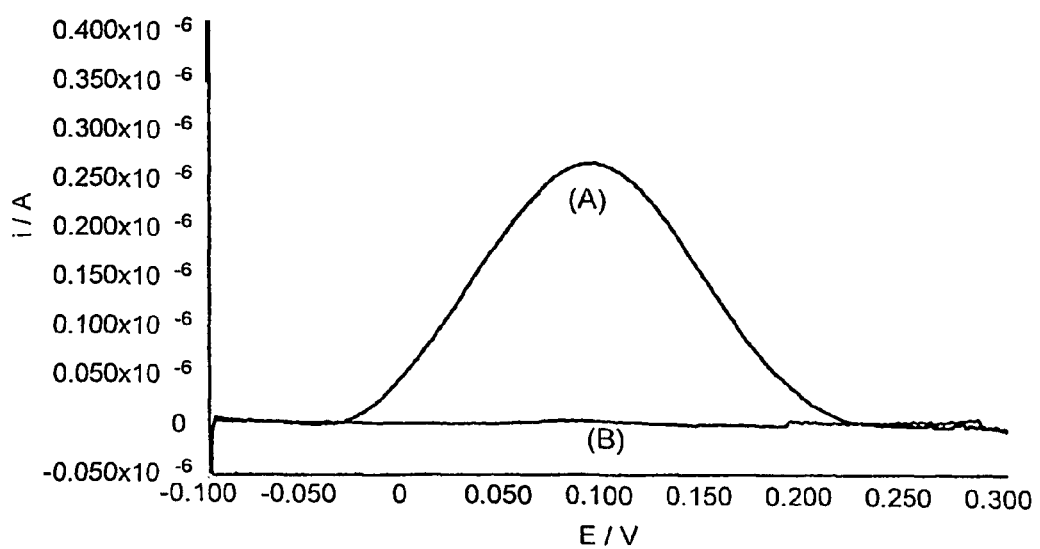

A digestion of FcU-BSA with papain was carried out as described above. The differential pulse voltammogram results are shown in FIG. 12 in which (a) is the trace for the digested product; (b) is the trace for the product of a no-papain control and (c) shows the data from (a) and (b) with baseline correction. The positive reaction has a peak position of 93 mV and a peak height of $2.62 \times 10^{-7}$ A; no peak was found in the no-papain control reaction.

EXAMPLE 5K

Digestion of FcU-casein with Trypsin

Figure 13A:
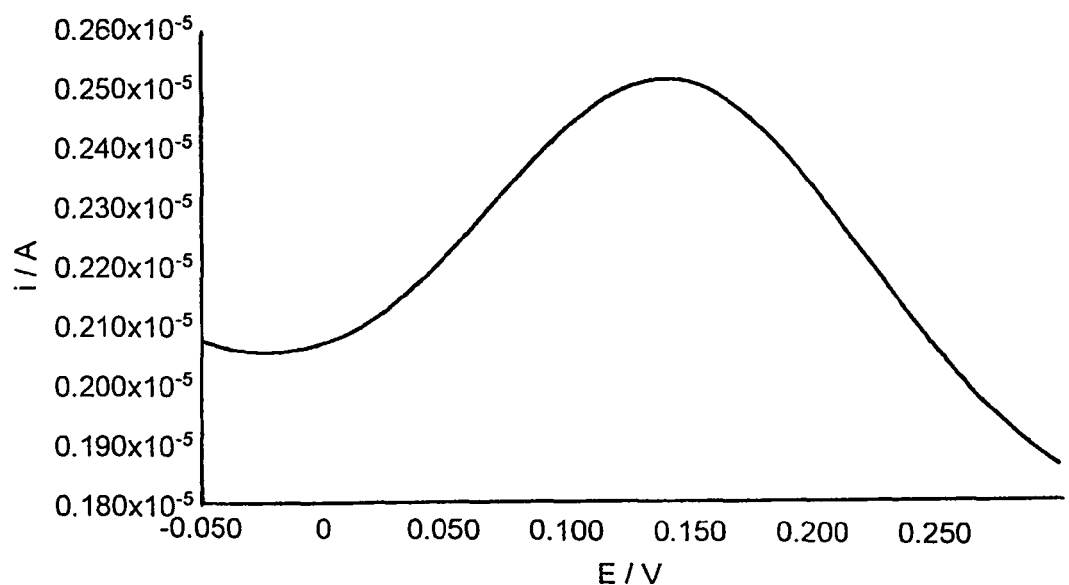
FIGS. 13a, 13b and 13c are differential pulse voltammograms of trypsin digestion products of FcU-casein as described in Example 5K.
Figure 13B:
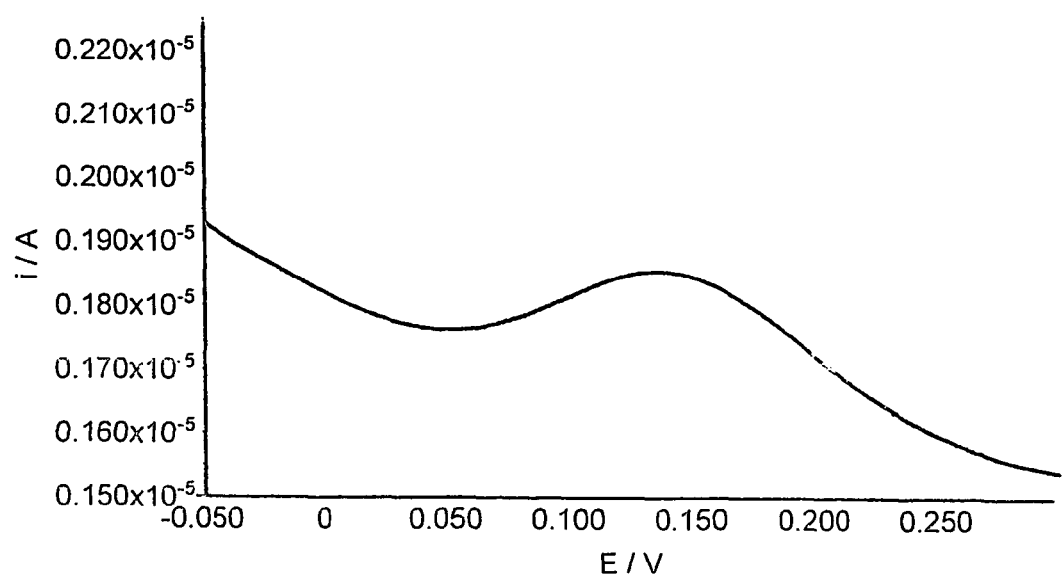
Figure 13C:
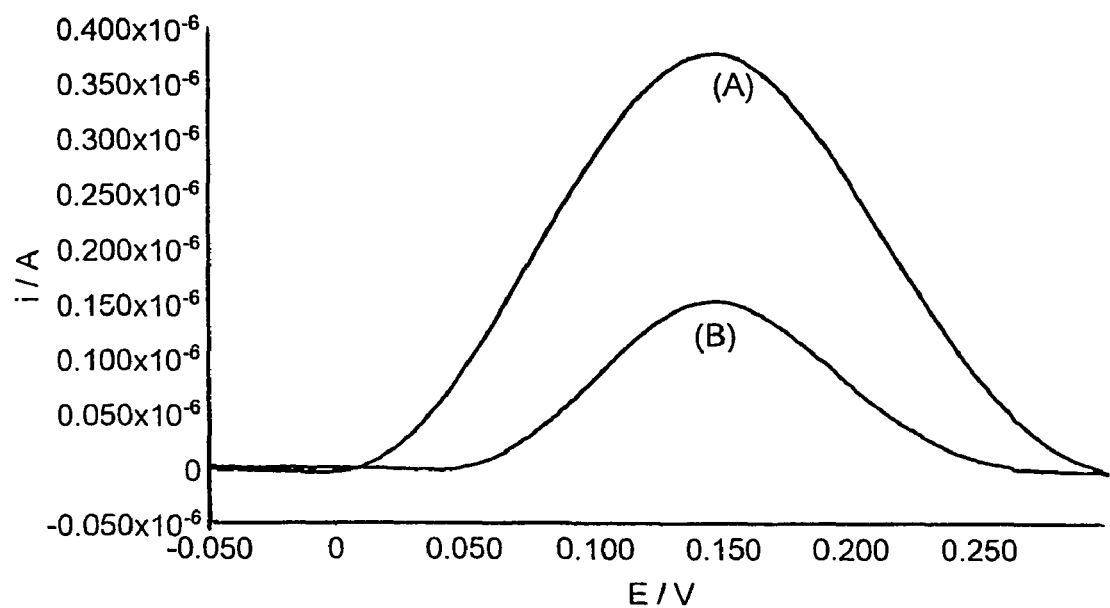

A digestion of FcU-casein with trypsin was carried out as described above. The differential pulse voltammogram results are shown in FIG. 13 in which (a) is the trace for the digested product; (b) is the trace for the product of a no-trypsin control and (c) shows the data from (a) and (b) with baseline correction. The positive reaction has a peak position of 148 mV and a peak height of $3.79 \times 10^{-7}$ A and the no-trypsin control reaction shows has a peak position of 147 mV and a peak height of $1.55 \times 10^{-7}$ A.

EXAMPLE 6

Variation Electrochemical Marker Signal with Enzyme Concentration

Figure 14:
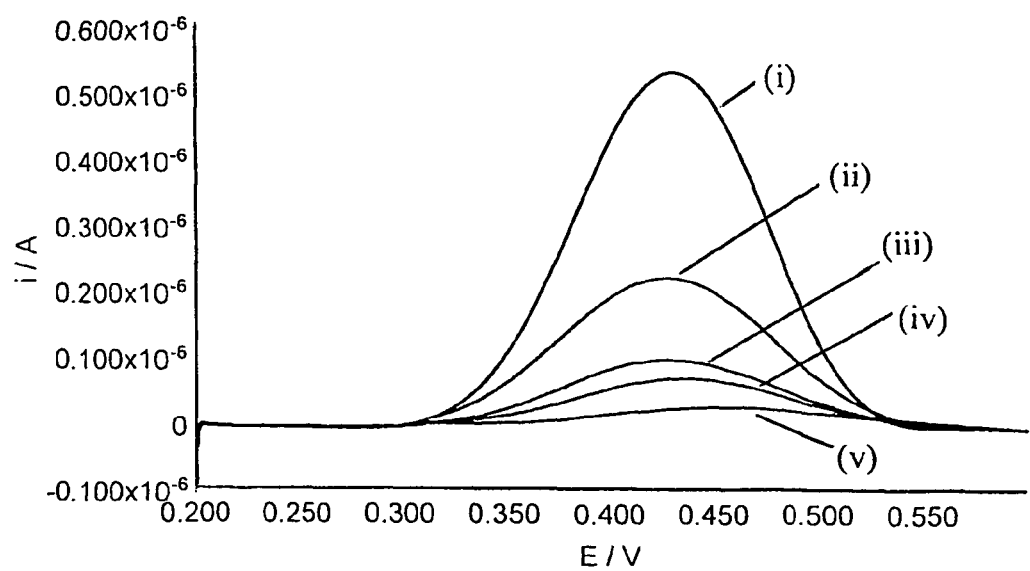
FIG. 14 shows overlaid differential pulse voltammograms of products of trypsin digestion of Fc-BSA carried out at various concentrations of enzyme as described in Example 6.

Five digestions of Fc-BSA with trypsin were carried out using the protocol described above. As described in the general protocol, 2 µl of enzyme was used for each 200 µl reaction; for reaction (i) 10 mg/ml enzyme solution was used; reaction (ii): 1 mg/ml; reaction (iii) 0.1 mg/ml; reaction (iv) 0.01 mg/ml and reaction (v) was a no-trypsin control. The differential pulse voltammogram results are shown in FIG. 14 with baseline correction. Reaction (i) has a peak position of 430 mV and a peak height of $5.42 \times 10^{-7}$ A, reaction (ii) has a peak position of 428 mV and a peak height of $2.29 \times 10^{-7}$ A, reaction (iii) has a peak position of 429 mV and a peak height of $1.04 \times 10^{-7}$ A, reaction (iv) has a peak position of 429 mV and a peak height of $7.53 \times 10^{8}$ A, the no-trypsin control reaction shows has a peak position of 448 mV and a peak height of $3.17 \times 10^{-9}$ A.

As is seen in FIG. 14, the magnitude of signal in the differential pulse voltammogram is strongly dependent on the concentration of enzyme present in the digestion experiment. A series of serial dilutions such as those described here may be used to provide data for a calibration standard curve. Such a curve is useful for quantifying enzyme levels or enzyme activities in an experimental sample of unknown protease content.

EXAMPLE 7

Variation Electrochemical Marker Signal with Incubation Time

Figure 15:
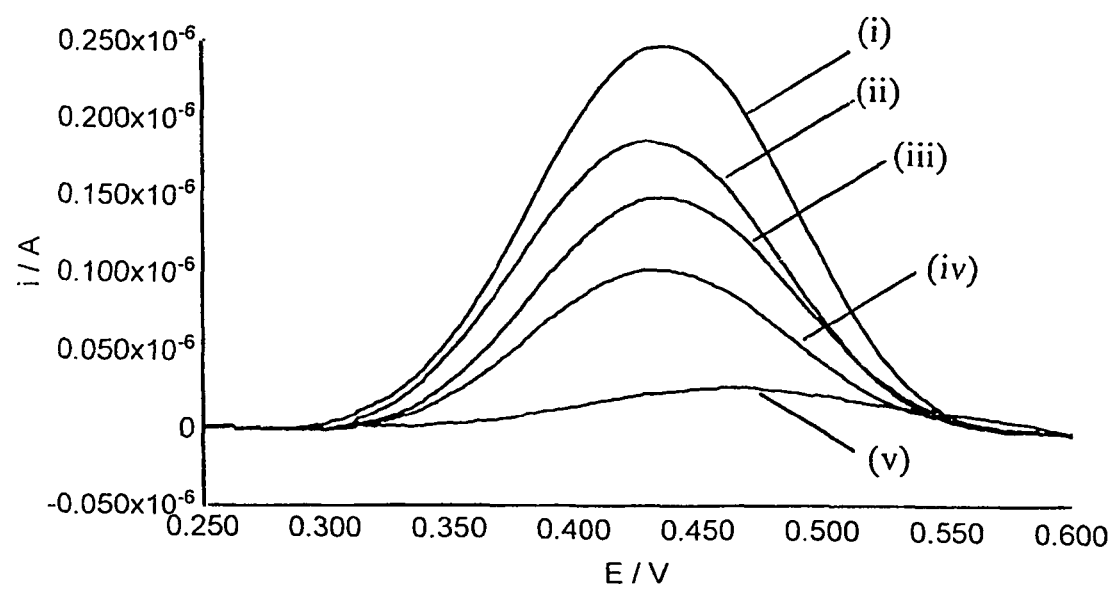
FIG. 15 shows overlaid differential pulse voltammograms of products of trypsin digestion of Fc-BSA carried out with various incubation times as described in Example 7.

Five digestions of Fc-BSA with trypsin were carried out using the protocol described above. In reaction (i) the incubation at 37° was carried out for 60 minutes, in reaction (ii) for 15 minutes, in reaction (iii) for 5 minutes, in reaction (iv) for 2 minutes and reaction (v) was a 0 minutes no-trypsin control. The differential pulse voltammogram results are shown in FIG. 15 with baseline correction. Reaction (i) has a peak position of 435 mV and a peak height of $2.49 \times 10^{-7}$ A, reaction (ii) has a peak position of 429 mV and a peak height of $1.88 \times 10^{-7}$ A, reaction (iii) has a peak position of 435 mV and a peak height of $1.57 \times 10^{-7}$ A, reaction (iv) has a peak position of 428 mV and a peak height of $1.04 \times 10^{-7}$ A, the no-trypsin control reaction shows has a peak position of 460 mV and a peak height of $2.11 \times 10^{-8}$ A.

As is seen in FIG. 15, the magnitude of signal in the differential pulse voltammogram is larger the longer the incubation is carried out.

EXAMPLE 8

The Effect of a Protease Inhibitor on Electrochemical Marker Signal

Figure 16:
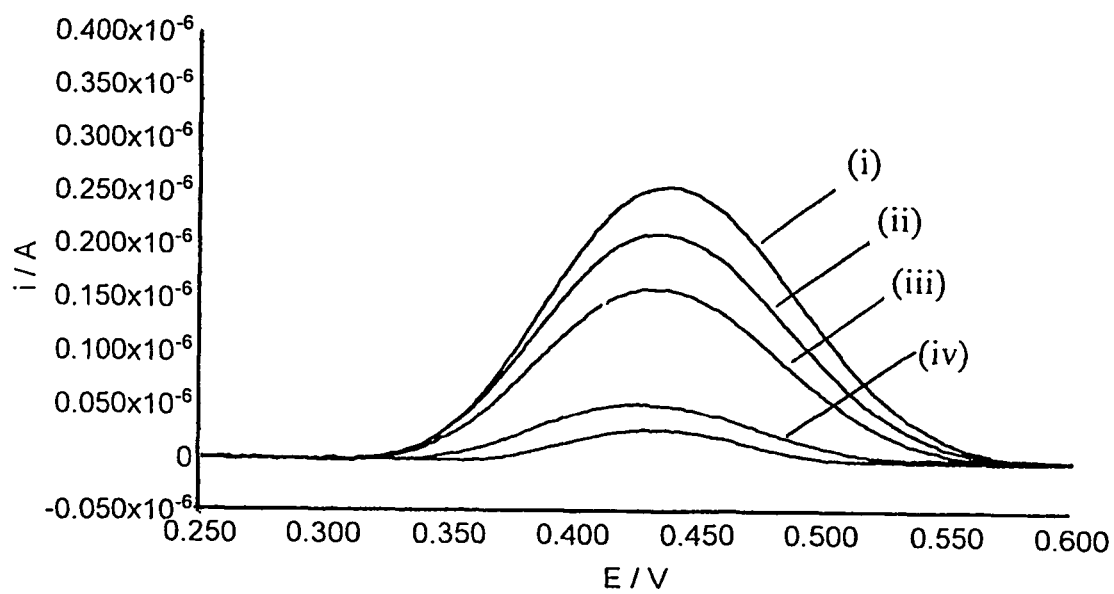
FIG. 16 shows overlaid differential pulse voltammograms of products of trypsin digestion of Fc-BSA carried out with various concentrations of protease inhibitor present as described in Example 8.

Five digestions of Fc-BSA with trypsin were carried out using the protocol described above. In addition, soybean trypsin inhibitor was added to reaction mixtures (i) to (iv). Solutions of the soybean trypsin inhibitor were prepared by resuspending inhibitor as supplied in deionised water to a concentration of 10 mg/ml and 1 mg/ml as appropriate. No inhibitor was added to reaction (i); 0.5 µl of 1 mg/ml inhibitor solution was added to reaction (ii); 0.51 of 10 mg/ml inhibitor was added to reaction (iii); 5 µl of 10 mg/ml inhibitor solution was added to reaction (iv) and 5 µl of 10 mg/ml inhibitor solution was added to a no-trypsin control reaction. The differential pulse voltammogram results are shown in FIG. 16 with baseline correction. Reaction (i) has a peak position of 439 mV and a peak height of $2.56 \times 10^{-7}$ A, reaction (ii) has a peak position of 435 mV and a peak height of $2.12 \times 10^{-7}$ A, reaction (iii) has a peak position of 430 mV and a peak height of $1.60 \times 10^{-7}$ A, reaction (iv) has a peak position of 426 mV and a peak height of $5.33 \times 10^{-8}$ A, the no-trypsin control reaction shows has a peak position of 429 mV and a peak height of $2.75 \times 10^{-8}$ A.

As is seen in FIG. 16, the magnitude of signal in the differential pulse voltammogram is strongly dependent on the concentration of inhibitor present in the digestion experiment. A series of serial dilutions such as those described here may be used to provide data for a calibration standard curve and such a curve is useful for quantifying inhibitor levels or inhibitor potencies in an experimental sample of unknown protease content. A calibration curve may also find utility in an assay for screening for potential protease inhibitors.

EXAMPLE 9

Amperometric Analysis of Digestion Reactions

Four digestion reactions were carried out with real-time amperometric analysis. Lyophilised enzymes were re-suspended to give a concentration of 10 mgml$^{-1}$. Tryspin was resuspended in HCl (1 mM, pH 3.0), papain and carboxypeptidase were resuspended in NaCl (100 mM). 75 µl of Fc-BSA solution (0.3-0.6 mgml$^{-1}$) was used per reaction. Each reaction was carried out in a total volume of 200 µl in the following buffers (final concentrations are given): 100 mM tris HCl pH7.8 for the trypsin reaction, 20 mM EDTA for the papain reaction, and 25 mM tris HCl pH7.5, 500 mM NaCl for the carboxypeptidase reaction. 2 µl enzyme (10 mgml$^{-1}$) was added to the 200 µl reaction mixture. The reaction products were analysed by amperometry in an apparatus as described above and shown in FIG. 1. The amperometry conditions were as set out in Tables 2 and 3.

TABLE 2

| Parameters for amperometry | |
|---|---|
| Parameter | |
| Pretreatment | |
| First conditioning potential (V) | 0 |
| Duration (s) | 0 |
| Equilibration time (s) | 4 |

TABLE 2-continued

Parameters for amperometry

| Parameter | |
|---|---|
| Measurement | |
| Interval time (>0.1 s) | 0.4 |
| Potential (V) | * |
| Duration (s) | 1200 |

* The potential applied to the working electrode was dependent on the ferrocenyl label and the pH of the buffer. Working electrode potentials for the enzyme/ferrocenylated substrate combinations are shown in Table 3:

TABLE 3

Electrode potentials used for amperometric detection of ferrocenyl labels

| Enzyme | Ferrocenyl label | Electrode potential* |
|---|---|---|
| Trypsin | Fc | 0.44 |
| Trypsin | FcU | 0.13 |
| Papain | FcU | 0.13 |

Figure 17:
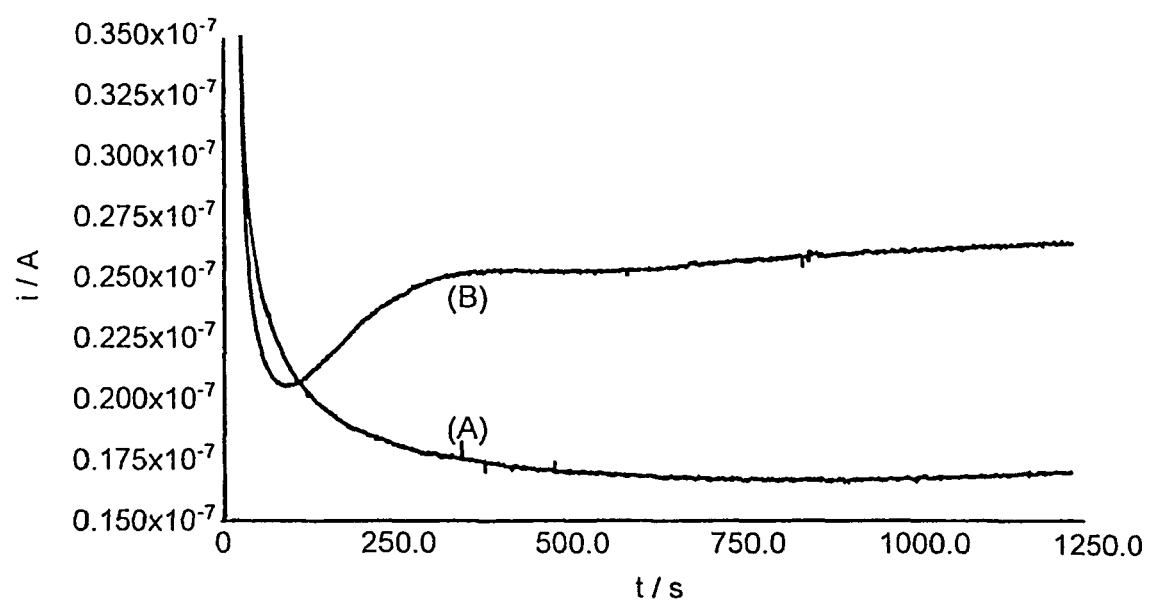
FIG. 17 shows overlaid amperometric traces of trypsin digestion of Fc-BSA with time.
Figure 18:
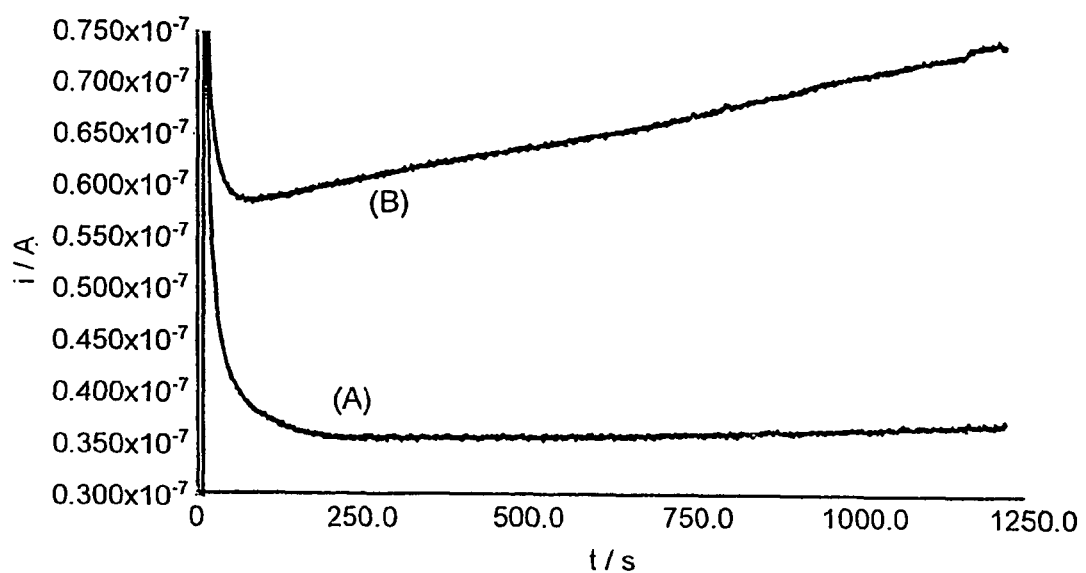
FIG. 18 shows overlaid amperometric traces of papain digestion of FcU-BSA with time.

The results of the amperometry experiments are shown in FIGS. 17 and 18.

In FIG. 17, there is shown the amperometric time course trace for the trypsin digestion of Fc-BSA. Line A shows the non-faradaic current response to application of the potential to the working electrode before enzyme addition. As the movement of the species present in the solution reaches a steady state, the current response appears to decay. Line B shows faradaic current response over time after addition of the enzyme, which takes place once the non-faradaic current response reaches an equilibrium. The increase in current shown in Line B appears to relate to enzymic digestion of the ferrocene labelled substrate.

In FIG. 18, there is shown the amperometric time course trace for the papain digestion of FcU-BSA. Line A shows the non-faradaic current response to application of the potential to the working electrode before enzyme addition. As the movement of the species present in the solution reaches a steady state, the current response appears to decay. Line B shows faradaic current response over time after addition of the enzyme which takes place once the non-faradaic current response reaches an equilibrium. The increase in current shown in Line B appears to relate to enzymic digestion of the ferrocene labelled substrate. The amperometric time course trace for the trypsin digestion of FcU-BSA is not illustrated in the drawings but was analogous.

As is seen from FIGS. 17 and 18, the electrochemically active marker allows a protease reaction to be followed in real-time as the reaction progresses without it being necessary to withdraw aliquots. A large amount of kinetic data may be extracted from plots such as those in FIGS. 17 and 18, enabling enzyme kinetics to be studied.

EXAMPLE 10

Aminopeptidase Assay

Figure 19A:
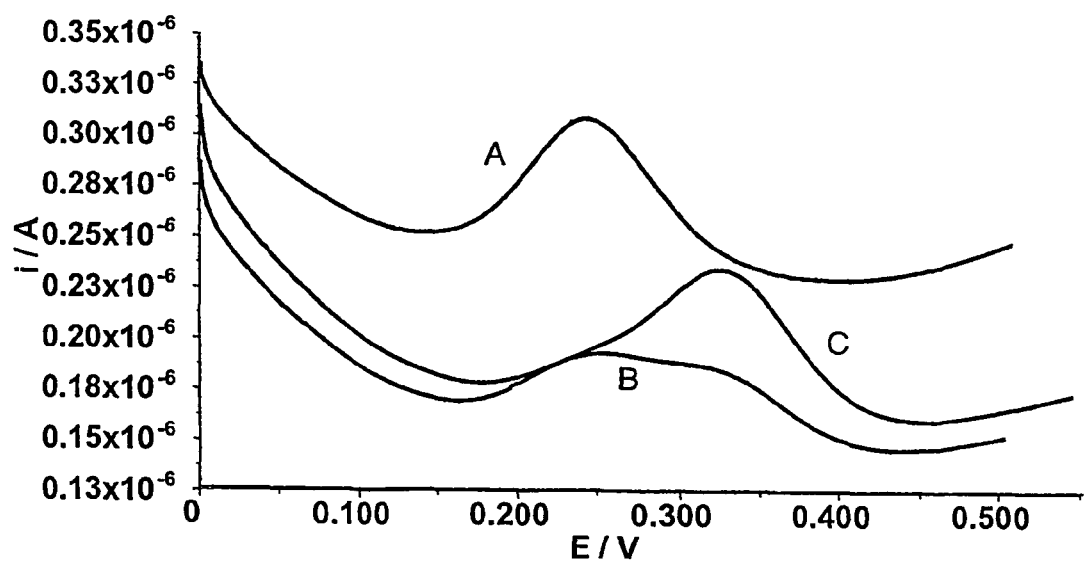
FIG. 19a shows overlaid differential pulse voltammetry traces for ferrocene labelled alanine (Fc-Ala) before and after aminopeptidase digestion as described in Example 10.
Figure 19B:
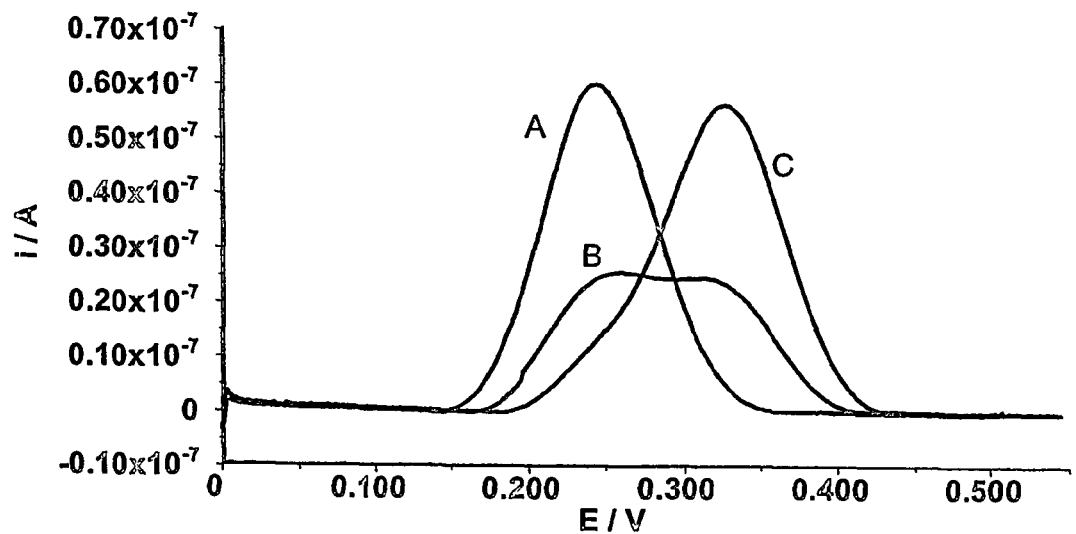

Aminopeptidase was obtained as 20 Uml$^{-1}$ in ammonium sulphate solution. The ferrocenylated alanine substrate of Example 4b was dissolved in ethanol at a 100 mM concentration. This was then diluted down to a working solution of 1 mM in 100 mM tris-HCl (pH 7.5). For a 200 μl volume, 195 μl of substrate solution (1 mM in tris-HCl/1% v/v ethanol) and 5 μl (0.01 U) of aminopeptidase were incubated for up to 15 minutes at 37° C. The sample was analysed by differential pulse voltammetry (DPV) before incubation, after 5 minutes incubation and after 15 minutes incubation. DPV was carried out as described in Example 1. Results are presented in FIG. 19a and FIG. 19b. FIG. 19a shows raw data and FIG. 19b shows the same data corrected for baseline using GPES MANAGER as explained in Example 5. Line A shows the voltammetry trace for ferrocenylated alanine before incubation with amino peptidase, line B shows the voltammetry trace after 5 minutes incubation with amino peptidase and line C shows the voltammetry trace after 15 minutes incubation with amino peptidase. It can be seen that digestion of the substrate causes the current peak potential to shift. After 15 minutes digestion, the shift is approximately 80 mV.

EXAMPLE 11

Elastase Assay

Figure 20A:
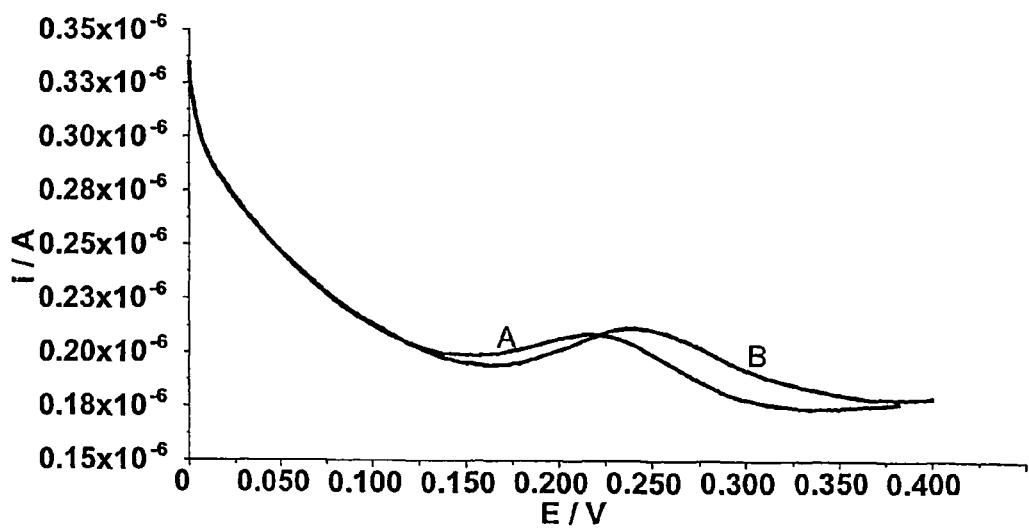
FIG. 20a shows overlaid differential pulse voltammetry traces for ferrocene labelled trialanine peptide (Ac-Ala-Ala-Ala-Fc) before and after elastase disgestion as described in Example 11.
Figure 20B:
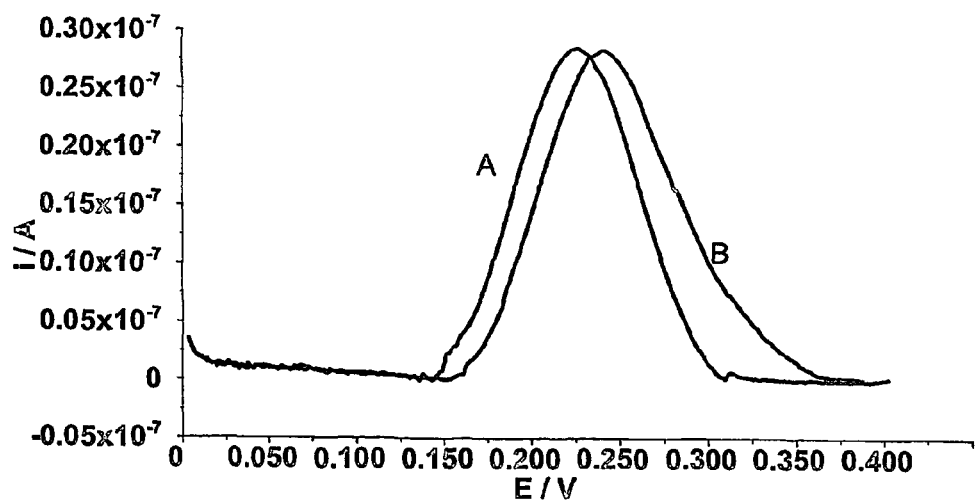

Elastase was obtained lyophilised and rehydrated in a 100 mM tris HCl buffer (pH 8.5) to 10 mg/ml. A 200μl aliquot of test sample was prepared to contain 50 μl ferrocene labelled tripeptide substrate (ferrocenylated trialanine peptide prepared as in Example 4c), 1μl elastase in tris HCl and the volume made up to 20011 with further addition of tris HCl buffer. The solution was incubated for 1 hour at 37° C. The sample was analysed by differential pulse voltammetry (DPV) before incubation and after 1 hour of incubation. DPV was carried out as described in Example 1. Results are presented in FIG. 20a and FIG. 20b. FIG. 20a shows raw data and FIG. 20b shows the same data corrected for baseline using GPES MANAGER as explained in Example 5. Line A shows the voltammetry trace for the substrate before incubation with elastase, and line B shows the voltammetry trace after 1 hour incubation with elastase. It can be seen that digestion of the substrate causes the current peak potential to shift. However, the shift is smaller than that shown in Example 10.

The invention claimed is:

1. A method for detecting protease activity in a sample solution comprising the steps of:
   i) contacting the sample solution with a protease substrate labeled with an electrochemically active marker, wherein the electrochemically active marker is a metallocene moiety,
   ii) providing conditions under which a protease present in the sample solution may degrade the protease substrate, wherein the protease is capable of recognizing the protease substrate, and
   iii) electrochemically determining information relating to the electrochemically active marker, thereby detecting the protease activity in the sample.

2. A method as claimed in claim 1 wherein the information relating to the electrochemically active marker is determined using voltammetry.

3. A method as claimed in claim 2 wherein the information relating to the electrochemically active marker is determined using differential pulse voltammetry.

4. A method as claimed in claim 1 wherein the information relating to the electrochemically active marker is determined using an amperometric technique.

5. A method as claimed in claim 1 wherein the information relating to the electrochemically active marker is determined using a technique that utilizes one or more electrodes that are functionally surrounded by a selectively permeable membrane.

6. A method as claimed in claim 1 wherein the electrochemically active marker is a ferrocene moiety.

7. A method as claimed in claim 1 wherein the electrochemically active marker is attached to the protease substrate through a linker.

8. A method as claimed in claim 1 wherein each protease substrate molecule is, on average, labeled with more than one electrochemically active marker molecule.

9. A method as claimed in claim 1 wherein the protease substrate labeled with an electrochemically active marker is a single amino acid labeled with an electrochemically active marker.

10. A method for detecting a disease in a subject the method comprising the method of claim 1 further comprising a step of comparing said protease activity with a level of protease activity that is diagnostic of a disease in a subject, thereby detecting a disease in a subject.

11. A method for detecting a pathogen the method comprising the method of claim 1 further comprising a step of comparing said protease activity with a level of protease activity that is diagnostic of the presence of a pathogen, thereby detecting a pathogen.

12. A method for screening for a protease inhibitor the method comprising the method of claim 1 further comprising a step of contacting the sample solution with a putative protease inhibitor.

* * * * *

SEQUENCE LISTING

```
<160> NUMBER OF SEQ ID NOS: 2

<210> SEQ ID NO 1
<211> LENGTH: 4
<212> TYPE: PRT
<213> ORGANISM: Artificial Sequence
<220> FEATURE:
<223> OTHER INFORMATION: Chymotrypsin substrate peptide sequence

<400> SEQUENCE: 1
```

```
Ala Ala Pro Phe
1

<210> SEQ ID NO 2
<211> LENGTH: 4
<212> TYPE: PRT
<213> ORGANISM: Artificial Sequence
<220> FEATURE:
<223> OTHER INFORMATION: Activated Factor X substrate recognition
      peptide sequence

<400> SEQUENCE: 2

Ile Glu Gly Arg
1
```